US006710173B1

(12) United States Patent
Binley et al.

(10) Patent No.: US 6,710,173 B1
(45) Date of Patent: Mar. 23, 2004

(54) STABILIZED VIRAL ENVELOPE PROTEINS AND USES THEREOF

(75) Inventors: James M. Binley, Brooklyn, NY (US); Norbert Schuelke, New City, NY (US); William C. Olson, Ossining, NY (US); Paul J. Maddon, Scarsdale, NY (US); John P. Moore, New York, NY (US)

(73) Assignees: Progenics Pharmaceuticals, Inc., Tarrytown, NY (US); Aaron Diamond AIDS Research Centre (ADARC), New York, NY (US)

( * ) Notice: Subject to any disclaimer, the term of this patent is extended or adjusted under 35 U.S.C. 154(b) by 0 days.

(21) Appl. No.: 09/602,864

(22) Filed: Jun. 23, 2000

Related U.S. Application Data

(60) Provisional application No. 60/141,168, filed on Jun. 25, 1999.

(51) Int. Cl.[7] ................................................ C07H 21/04

(52) U.S. Cl. ................................ 536/23.72; 424/188.1; 424/208.1

(58) Field of Search ........................... 424/188.1, 208.1; 536/23.72

(56) References Cited

U.S. PATENT DOCUMENTS 5,886,163 A 3/1999 Hasel et al.
5,935,579 A 8/1999 Habeshaw et al.

OTHER PUBLICATIONS

Murphy, F. A., 1996, "Virus taxonomy", in *Fields Virology*, Third Edition, Fields, B. N., et al., eds., Lippincott–Raven Publishers, Philadelphia, pp. 40 and 41.*

Reitter, J. N., et al., 1998, "A role for carbohydrates in immune evasion in AIDS", Nature Med. 4(6):679–684.*

Moore, J. P., et al., 1994(a), "Probing the structure of the human immunodeficiency virus surface glycoprotein gp120 with a panel of monoclonal antibodies", J. Virol. 68(1):469–484.*

Mitchell, W. M., et al., 1998, "Inactivation of a common epitope responsible for the induction of antibody–dependent enhancement of HIV", AIDS 12:147–156.*

Burton, D. R. and J. P. Moore, 1998, "Why do we not have an HIV vaccine and how can we make one?", Nature Med. Vaccine Suppl. 4(5):495–498.*

Johnston, M. I. and J. Flores, 2001, "Progress in HIV vaccine development", Curr. Opin. Pharmacol. 1(5):504–510.*

Moore, J. P., et al., 1994(b), "Immunological evidence for interactions between the first, second, and fifth conserved domains fo the gp120 surface glycoprotein of human immunodeficiency virus type 1", J. Virol. 68(11):6836–6847.*

(List continued on next page.)

*Primary Examiner*—Laurie Scheiner
*Assistant Examiner*—Jeffrey S. Parkin
(74) *Attorney, Agent, or Firm*—John P. White; Cooper & Dunham LLP

(57) ABSTRACT

This invention provides an isolated nucleic acid which comprises a nucleotide segment having a sequence encoding a viral envelope protein comprising a viral surface protein and a corresponding viral transmembrane protein wherein the viral envelope protein contains one or more mutations in amino acid sequence that enhance the stability of the complex formed between the viral surface protein and transmembrane protein. This invention also provides a viral envelope protein comprising a viral surface protein and a corresponding viral transmembrane protein wherein the viral envelope protein contains one or more mutations in amino acid sequence that enhance the stability of the complex formed between the viral surface protein and transmembrane protein. This invention further provides methods of treating HIV-1 infection.

30 Claims, 20 Drawing Sheets

OTHER PUBLICATIONS

Helseth, E., et al., 1991, "Human immunodeficiency virus type 1 gp120 envelope glycoprotein regions important for association with the gp41 transmembrane glycoprotein", J. Virol. 65(4):2119–2123.*

Maerz, A. L., et al., 2001, "Functional analysis of the disulfide–bonded loop/chain reversal region of human immunodeficiency virus type 1 gp41 reveals a critical role in gp120–gp41 association", J. Virol. 75(14):6635–6644.*

Joy, A. K., et al., 1999, "Can HIV infection be prevented with a vaccine?", Drugs R&D 6:431–440.

Haynes, B. F., 1996, "HIV vaccines: where are we and where are we going?", Lancet 348:933–937.

Barouch, D. H., et al., 2002, "Eventual AIDS vaccine failure in a rhesus monkey by viral escape from cytotoxic T lymphocytes", Nature 415:335–339.

Barouch, D. H. and N. L. Letvin, 2000, "DNA vaccination for HIV–1 and SIV", Intervirol. 43:282–287.

Atwell, et al., (1997) "Stable Heterodimers form Remodeling the Domain Interface of a Homodimer using a Phage Display Library," J. Mol. Biol. 270:26–35 (Exhibit 1).

Cao, et al., (1997) "Replication and Neutralization of Human Immunodeficiency Virus Type 1 Lacking the V1 and V2 Variable Loops of the gp120 Evenlope Glycoprotein," J. Virol. 71:9809–9812 (Exhibit 2).

Edinger, et al., (1999) "Functional Dissection of CCR5 Coreceptor Function Through the use of CD4–Independent Simian Immunodeficiency Virus Strains," J. Virol. 73:4062 (Exhibit 3).

Fouts, et al., (1998) "Interactions of Polyclonal and Monoclonal Anti–Glycoprotein 120 Antibodies with Oligomeric Glycoprotein 120–Glycoprotein 41 Complexes of a Primary HIV Type 1 Isolate: Relationship to Neutralization," AIDS Res. Human Retrovir. 14:591 (Exhibit 4).

Fouts, et al., (1997) "Neutralization of the Human Immunodeficiency Virus Type 1 Primary Isolate JR–FL by Human Monoclonal Antibodies Correlates with Antibody Binding to the Oligomeric Form of the Envelope glycoprotein Complex," J. Virol. 71:2779 (Exhibit 5).

Gallaher, et al., "A General Model for the Surface Glycoproteins of HIV and Other Retroviruses," AIDS Res. Human Retrovir. 11:191 (Exhibit 6).

Moore, et al., (1994) "Probing the Structure of the Human Immunodeficiency Virus Surface Glycoprotein gp120 with a Panel of Monoclonal Antibodies," J. Virol. 68:469 (Exhibit 7).

Parren, er al., (1997) "HIV–1 antibody—debris or virion?" Nat. Med. 3:366 (Exhibit 8).

Parren, et al., (1998) "Neutralization of Human Immunodeficiency Virus Type 1 by Antibody to gp120 Is Determined Primarily by Occupancy of Sites on the Virion Irrespective of Epitope Specificity," J. Virol. 72:3512 (Exhibit 9).

Reitter, et al., (1998) "A Role For Carbohydrates in Immune Evasion in AIDS," Nat. Med., 4:679–684 (Exhibit 10).

Schulz, et al., (1992) "Conserved Structural Features in the Interaction Between Retroviral Surface and Transmembrane Glycoproteins?" AIDS Res. Hum. Retrovirus, 8(9):1571–1580 (Exhibit 11).

McInerney, T.L. et al., (1998), Mutation–directed chemical cross–linking of Human Immunodeficiency Virus Type 1 gp41 oligomers, *J. Virol.* 72:1523–1533 (Exhibit 2).

Mitchell, W.M. et al., (1998), Inactivation of a common epitope responsible for the induction of antibody–dependent enhancement of HIV, *AIDS* 12:147–156 (Exhibit 3).

Stamatatos, L. et al., (1994), Differential regulation of cellular tropism and sensitivity to soluble CD4 neutralization by the envelope gp120 of Human Immunodeficiency Virus Type 1, *J. Virol.* 68:4973–4979 (Exhibit 4).

Burton, D.R. et al. (1994) Efficient neutralization of primary isolates of HIV–1 by a recombinant human monoclonal antibody. Science 266: 1024–1027.

Labranche, C.C. et al. (1994) Biological, molecular, and structural analysis of a cytopathic variant from a molecularly cloned simian immunodeficiency virus. J. Virol. 68(9): 5509–5522.

Labranche, C.C. et al. (1994) Biological, molecular, and structural analysis of a cytopathic variant from a molecularly cloned simian immunodeficiency virus. J. Virol. 68(11): 7665–7667.

Trkola, A. et al. (1996) Human monoclonal antibody 2G12 defines a distinctive neutralization epitope on the gp120 glycoprotein of human immunodeficiency virus type 1. J. Virol. 70(2): 1100–1108.

Binley, J., et al., (2000) "A Recombinant Human Immunodeficiency Virus Type 1 Envelope Glycoprotein Complex Stabilized By An Intermolecular Disulfide Bond Between The GP 120 and GP 41 Subunits Is An Antigenic Mimic Of The Trimeric Viron–Associated Structure", Journal of Virology, vol. 74, No. 2, 627–643 (Exhibit B).

Farzan, M., et al. (1998) "Stabilization Of Human Immunodeficiency Virus Type 1 Envelope Glycoprotein Trimers By Disulfide Bonds Introduced Into The GP 41 Glycoprotein Ectodomain", Journal of Virology, vol. 72, No. 9, 7620–7625 (Exhibit C).

* cited by examiner

| | D580C | W587C | T596C | V599C | P600C | W601C |
|---|---|---|---|---|---|---|
| V35C | 0.45 | 0.40 | 0.35 | 0.30 | 0.40 | 0.30 |
| Y39C | 0.35 | 0.30 | 0.60 | 0.45 | 0.45 | N.D. |
| W44C | 0.45 | 0.45 | 0.65 | 0.50 | 0.65 | 0.45 |

gp120 C5

| | D580C | W587C | T596C | V599C | P600C | W601C |
|---|---|---|---|---|---|---|
| P484C | 0.35 | 0.30 | 0.45 | 0 | 0 | 0 |
| G486C | 0 | 0 | 0.25 | 0.20 | 0.30 | 0 |
| A488C | 0 | 0 | 0.05 | 0 | 0 | 0 |
| P489C | 0 | 0.10 | 0.30 | 0.15 | 0.05 | 0 |
| T490C | 0 | 0.15 | 0.55 | 0.25 | 0.25 | 0.10 |
| A492C | 0.05 | 0 | 0.75 | 0.50 | 0.10 | 0.25 |

| IgG1b12 (CD4bs) | | | CD4IgG2 (CD4) | | | 2G12 (C3-V4) | | | 19b (V3) | | | 83.1 (V3) | | |
|---|---|---|---|---|---|---|---|---|---|---|---|---|---|---|
| wt | SOS | 44 596 | wt | SOS | 44 596 | wt | SOS | 44 596 | wt | SOS | 44 596 | wt | SOS | 44 596 |
| 1 | 2 | 3 | 4 | 5 | 6 | 7 | 8 | 9 | 10 | 11 | 12 | 13 | 14 | 15 |

| M90 (C1D) | | | C11 (C1-C5) | | | 23A (C5L) | | | G3-42 (C4-V3) | | | G3-519 (C4L) | | |
|---|---|---|---|---|---|---|---|---|---|---|---|---|---|---|
| wt | SOS | 44 596 | wt | SOS | 44 596 | wt | SOS | 44 596 | wt | SOS | 44 596 | wt | SOS | 44 596 |
| 1 | 2 | 3 | 4 | 5 | 6 | 7 | 8 | 9 | 10 | 11 | 12 | 13 | 14 | 15 |

| 17b | | | 17b/sCD4 | | | A32 | | | A32/sCD4 | | |
|---|---|---|---|---|---|---|---|---|---|---|---|
| wt | SOS | 44 596 | wt | SOS | 44 596 | wt | SOS | 44 596 | wt | SOS | 44 596 |
| 1 | 2 | 3 | 4 | 5 | 6 | 7 | 8 | 9 | 10 | 11 | 12 |

140→
120→

A

| wt ΔV1V2*V3 | | CC ΔV1V2*V3 | | wt ΔV1V2*V3 N357Q N398Q | | CC ΔV1V2*V3 N357Q N398Q | | wt | | **envelope protein** |
|---|---|---|---|---|---|---|---|---|---|---|
| 2G12 | F91 | 2G12 | F91 | 2G12 | F91 | 2G12 | F91 | F91 | F91 | **antibody** |
| 1 | 2 | 3 | 4 | 5 | 6 | 7 | 8 | 9 | 10 | **lane** |

←140
←120
←90
←85

B

| wt | ΔV1 | | ΔV2 | | ΔV3 | | ΔV1V2' | | ΔV1V2* | | ΔV1V2*V3 | | **protein** |
|---|---|---|---|---|---|---|---|---|---|---|---|---|---|
| CC | | CC | | CC | | CC | | CC | | CC | | CC | **cysteines** |
| 1 | 2 | 3 | 4 | 5 | 6 | 7 | 8 | 9 | 10 | 11 | 12 | 13 | **lane** |

*FIGURE 13A*

HIV-1$_{JR-FL}$ SOS gp140

```
(a)
1     GTAGAAAAGTTGTGGGTCACAGTCTATTATGGGGTACCTGTGTGGAAAGA
51    AGCAACCACCACTCTATTTTGTGCATCAGATGCTAAAGCATATGATACAG
101   AGGTACATAATGTTTGGGCCACACATGCCTGTGTACCCACAGACCCCAAC
151   CCACAAGAAGTAGTATTGGAAAATGTAACAGAACATTTTAACATGTGGAA
201   AAATAACATGGTAGAACAGATGCAGGAGGATATAATCAGTTTATGGGATC
251   AAAGCCTAAAGCCATGTGTAAAATTAACCCCACTCTGTGTTACTTTAAAT
301   TGCAAGGATGTGAATGCTACTAATACCACTAATGATAGCGAGGGAACGAT
351   GGAGAGAGGAGAAATAAAAAACTGCTCTTTCAATATCACCACAAGCATAA
401   GAGATGAGGTGCAGAAAGAATATGCTCTTTTTTATAAACTTGATGTAGTA
451   CCAATAGATAATAATAATACCAGCTATAGGTTGATAAGTTGTGACACCTC
501   AGTCATTACACAGGCCTGTCCAAAGATATCCTTTGAGCCAATTCCCATAC
551   ATTATTGTGCCCCGGCTGGTTTTGCGATTCTAAAGTGTAATGATAAGACG
601   TTCAATGGAAAAGGACCATGTAAAAATGTCAGCACAGTACAATGTACACA
651   TGGAATTAGGCCAGTAGTATCAACTCAACTGCTGCTAAATGGCAGTCTAG
701   CAGAAGAAGAGGTAGTAATTAGATCTGACAATTTCACGAACAATGCTAAA
751   ACCATAATAGTACAGCTGAAAGAATCTGTAGAAATTAATTGTACAAGACC
801   CAACAACAATACAAGAAAAAGTATACATATAGGACCAGGGAGAGCATTTT
851   ATACTACAGGAGAAATAATAGGAGATATAAGACAAGCACATTGTAACATT
901   AGTAGAGCAAAATGGAATGACACTTTAAAACAGATAGTTATAAAATTAAG
951   AGAACAATTTGAGAATAAAACAATAGTCTTTAATCACTCCTCAGGAGGGG
1001  ACCCAGAAATTGTAATGCACAGTTTTAATTGTGAAGGAGAATTTTTCTAC
1051  TGTAATTCAACACAACTGTTTAATAGTACTTGGAATAATAATACTGAAGG
1101  GTCAAATAACACTGAAGGAAATACTATCACACTCCCATGCAGAATAAAAC
1151  AAATTATAAACATGTGGCAGGAAGTAGGAAAAGCAATGTATGCCCCTCCC
1201  ATCAGAGGACAAATTAGATGTTCATCAAATATTACAGGGCTGCTATTAAC
1251  AAGAGATGGTGGTATTAATGAGAATGGGACCGAGATCTTCAGACCTGGAG
1301  GAGGAGATATGAGGGACAATTGGAGAAGTGAATTCTATAAATATAAAGTA
1351  GTAAAAATTGAACCATTAGGAGTAGCACCCACCAAGTGCAAGAGAAGAGT
1401  GGTGCAAAGAGAAAAAAGAGCAGTGGGAATAGGAGCTGTGTTCCTTGGGT
1451  TCTTGGGAGCAGCAGGAAGCACTATGGGCGCAGCGTCAATGACACTGACG
1501  GTACAGGCCAGACTATTATTGTCTGGTATAGTGCAACAGCAGAACAATTT
1551  GCTGAGGGCTATTGAGGCGCAACAGCGTATGTTGCAACTCACAGTCTGGG
1601  GCATCAAGCAGCTCCAGGCAAGAGTCCTGGCTGTGGAAAGATACCTAGGG
1651  GATCAACAGCTCCTGGGGATTTGGGGTTGCTCTGGAAAACTCATTTGCTG
1701  CACTGCTGTGCCTTGGAATGCTAGTTGGAGTAATAAATCTCTAGATAGGA
1751  TTTGGAATAACATGACCTGGATGGAGTGGGAAAGAGAAATTGACAATTAC
1801  ACAAGCGAAATATACACACTAATTGAAGAATCGCAGAACCAACAAGAAAA
1851  GAATGAACAAGAATTATTGGAATTAGATAAATGGGCAAGTTTGTGGAATT
1901  GGTTTGACATAACAAACTGGCTGTGGTAT
```

*FIGURE 13B*

```
30   VEKLWVTVYY GVPVWKEATT TLFCASDAKA YDTEVHNVWA THACVPTDPN
80   PQEVVLENVT EHFNMWKNNM VEQMQEDIIS LWDQSLKPCV KLTPLCVTLN
130  CKDVNATNTT NDSEGTMERG EIKNCSFNIT TSIRDEVQKE YALFYKLDVV
180  PIDNNNTSYR LISCDTSVIT QACPKISFEP IPIHYCAPAG FAILKCNDKT
230  FNGKGPCKNV STVQCTHGIR PVVSTQLLLN GSLAEEEVVI RSDNFTNNAK
280  TIIVQLKESV EINCTRPNNN TRKSIHIGPG RAFYTTGEII GDIRQAHCNI
330  SRAKWNDTLK QIVIKLREQF ENKTIVFNHS SGGDPEIVMH SFNCEGEFFY
380  CNSTQLFNST WNNNTEGSNN TEGNTITLPC RIKQIINMWQ EVGKAMYAPP
430  IRGQIRCSSN ITGLLLTRDG GINENGTEIF RPGGGDMRDN WRSEFYKYKV
480  VKIEPLGVAP TKCKRRVVQR EKRAVGIGAV FLGFLGAAGS TMGAASMTLT
530  VQARLLLSGI VQQQNNLLRA IEAQQRMLQL TVWGIKQLQA RVLAVERYLG
580  DQQLLGIWGC SGKLICCTAV PWNASWSNKS LDRIWNNMTW MEWEREIDNY
630  TSEIYTLIEE SQNQQEKNEQ ELLELDKWAS LWNWFDITNW LWY
```

*FIGURE 14A*

HIV-1$_{JR-FL}$ ΔV1V2* SOS gp140

(a)

1 GTAGAAAAGTTGTGGGTCACAGTCTATTATGGGGTACCTGTGTGGAAAGA
51 AGCAACCACCACTCTATTTTGTGCATCAGATGCTAAAGCATATGATACAG
101 AGGTACATAATGTTTGGGCCACACATGCCTGTGTACCCACAGACCCCAAC
151 CCACAAGAAGTAGTATTGGAAAATGTAACAGAACATTTTAACATGTGGAA
201 AAATAACATGGTAGAACAGATGCAGGAGGATATAATCAGTTTATGGGATC
251 AAAGCCTAAAGCCATGTGTAAAATTAACCCCACTCTGTGGTGCAGGATGT
301 GACACCTCAGTCATTACACAGGCCTGTCCAAAGATATCCTTTGAGCCAAT
351 TCCCATACATTATTGTGCCCCGGCTGGTTTTGCGATTCTAAAGTGTAATG
401 ATAAGACGTTCAATGGAAAAGGACCATGTAAAAATGTCAGCACAGTACAA
451 TGTACACATGGAATTAGGCCAGTAGTATCAACTCAACTGCTGCTAAATGG
501 CAGTCTAGCAGAAGAAGAGGTAGTAATTAGATCTGACAATTTCACGAACA
551 ATGCTAAAACCATAATAGTACAGCTGAAAGAATCTGTAGAAATTAATTGT
601 ACAAGACCCAACAACAATACAAGAAAAAGTATACATATAGGACCAGGGAG
651 AGCATTTTATACTACAGGAGAAATAATAGGAGATATAAGACAAGCACATT
701 GTAACATTAGTAGAGCAAAATGGAATGACACTTTAAAACAGATAGTTATA
751 AAATTAAGAGAACAATTTGAGAATAAAACAATAGTCTTTAATCACTCCTC
801 AGGAGGGGACCCAGAAATTGTAATGCACAGTTTTAATTGTGGAGGAGAAT
851 TTTTCTACTGTAATTCAACACAACTGTTTAATAGTACTTGGAATAATAAT
901 ACTGAAGGGTCAAATAACACTGAAGGAAATACTATCACACTCCCATGCAG
951 AATAAAACAAATTATAAACATGTGGCAGGAAGTAGGAAAAGCAATGTATG
1001 CCCCTCCCATCAGAGGACAAATTAGATGTTCATCAAATATTACAGGGCTG
1051 CTATTAACAAGAGATGGTGGTATTAATGAGAATGGGACCGAGATCTTCAG
1101 ACCTGGAGGAGGAGATATGAGGGACAATTGGAGAAGTGAATTATATAAAT
1151 ATAAAGTAGTAAAAATTGAACCATTAGGAGTAGCACCCACCAAGTGCAAG
1201 AGAAGAGTGGTGCAAAGAGAAAAAAGAGCAGTGGGAATAGGAGCTGTGTT
1251 CCTTGGGTTCTTGGGAGCAGCAGGAAGCACTATGGGCGCAGCGTCAATGA
1301 CACTGACGGTACAGGCCAGACTATTATTGTCTGGTATAGTGCAACAGCAG
1351 AACAATTTGCTGAGGGCTATTGAGGCGCAACAGCGTATGTTGCAACTCAC
1401 AGTCTGGGGCATCAAGCAGCTCCAGGCAAGAGTCCTGGCTGTGGAAAGAT
1451 ACCTAGGGGATCAACAGCTCCTGGGGATTTGGGGTTGCTCTGGAAAACTC
1501 ATTTGCTGCACTGCTGTGCCTTGGAATGCTAGTTGGAGTAATAAATCTCT
1551 GGATAGGATTTGGAATAACATGACCTGGATGGAGTGGGAAAGAGAAATTG
1601 ACAATTACACAAGCGAAATATACACCCTAATTGAAGAATCGCAGAACCAA
1651 CAAGAAAAGAATGAACAAGAATTATTGGAATTAGATAAATGGGCAAGTTT
1701 GTGGAATTGGTTTGACATAACAAACTGGCTGTGGTAT

30 VEKLWVTVYY GVPVWKEATT TLFCASDAKA YDTEVHNVWA THACVPTDPN
80 PQEVVLENVT EHFNMWKNNM VEQMQEDIIS LWDQSLKPCV KLTPLCGAGC
130 DTSVITQACP KISFEPIPIH YCAPAGFAIL KCNDKTFNGK GPCKNVSTVQ
180 CTHGIRPVVS TQLLLNGSLA EEEVVIRSDN FTNNAKTIIV QLKESVEINC
230 TRPNNNTRKS IHIGPGRAFY TTGEIIGDIR QAHCNISRAK WNDTLKQIVI
280 KLREQFENKT IVFNHSSGGD PEIVMHSFNC GGEFFYCNST QLFNSTWNNN
330 TEGSNNTEGN TITLPCRIKQ IINMWQEVGK AMYAPPIRGQ IRCSSNITGL
380 LLTRDGGINE NGTEIFRPGG GDMRDNWRSE LYKYKVVKIE PLGVAPTKCK
430 RRVVQREKRA VGIGAVFLGF LGAAGSTMGA ASMTLTVQAR LLLSGIVQQQ
480 NNLLRAIEAQ QRMLQLTVWG IKQLQARVLA VERYLGDQQL LGIWGCSGKL
530 ICCTAVPWNA SWSNKSLDRI WNNMTWMEWE REIDNYTSEI YTLIEESQNQ
580 QEKNEQELLE LDKWASLWNW FDITNWLWY

*FIGURE 15A*

HIV-$1_{JR-FL}$ ΔV3 SOS gp140

(a)

```
1     GTAGAAAAGTTGTGGGTCACAGTCTATTATGGGGTACCTGTGTGGAAAGA
51    AGCAACCACCACTCTATTTTGTGCATCAGATGCTAAAGCATATGATACAG
101   AGGTACATAATGTTTGGGCCACACATGCCTGTGTACCCACAGACCCCAAC
151   CCACAAGAAGTAGTATTGGAAAATGTAACAGAACATTTTAACATGTGGAA
201   AAATAACATGGTAGAACAGATGCAGGAGGATATAATCAGTTTATGGGATC
251   AAAGCCTAAAGCCATGTGTAAAATTAACCCCACTCTGTGTTACTTTAAAT
301   TGCAAGGATGTGAATGCTACTAATACCACTAATGATAGCGAGGGAACGAT
351   GGAGAGAGGAGAAATAAAAAACTGCTCTTTCAATATCACCACAAGCATAA
401   GAGATGAGGTGCAGAAAGAATATGCTCTTTTTTATAAACTTGATGTAGTA
451   CCNATAGATAATAATAATACCAGCTATAGGTTGATAAGTTGTGACACCTC
501   AGTCATTACACAGGCCTGTCCAAAGATATCCTTTGAGCCAATTCCCATAC
551   ATTATTGTGCCCCGGCTGGTTTTGCGATTCTAAAGTGTAATGATAAGACG
601   TTCAATGGAAAAGGNCCATGTAAAAATGTCAGCACAGTNCAATGTACACA
651   TGGAATTAGGCCAGTAGTATCAACTCAACTGCTGCTAAATGGCAGTCTAG
701   CAGAAGAAGAGGTAGTAATTAGATCTGACAATTTCACGAACAATGCTAAA
751   ACCATAATAGTACAGCTGAAAGAATCTGTAGAAATTAATTGTACAAGACC
801   CAACAACAATGGAGCCGGCGATATAAGACAAGCACATTGTAACATTAGTA
851   GAGCAAAATGGAATGACACTTTAAAACAGATAGTTATAAAATTAAGAGAA
901   CAATTTGAGAATAAAACAATAGTCTTTAATCACTCCTCAGGAGGGGACCC
951   AGAAATTGTAATGCACAGTTTTAATTGTGGAGGAGAATTTTTCTACTGTA
1001  ATTCAACACAACTGTTTAATAGTACTTGGAATAATAATACTGAAGGGTCA
1051  AATAACACTGAAGGAAATACTATCACACTCCCATGCAGAATAAAACAAAT
1101  TATAAACATGTGGCAGGAAGTAGGAAAAGCAATGTATGCCCCTCCCATCA
1151  GAGGACAAATTAGATGTTCATCAAATATTACAGGGCTGCTATTAACAAGA
1201  GATGGTGGTATTAATGAGAATGGGACCGAGATCTTCAGACCTGGAGGAGG
1251  AGATATGAGGGACAATTGGAGAAGTGAATTATATAAATATAAAGTAGTAA
1301  AAATTGAACCATTAGGAGTAGCACCCACCAAGTGCAAGAGAAGAGTGGTG
1351  CAAAGAGAAAAAAGAGCAGTGGGAATAGGAGCTGTGTTCCTTGGGTTCTT
1401  GGGAGCAGCAGGAAGCACTATGGGCGCAGCGTCAATGACACTGACGGTAC
1451  AGGCCAGACTATTATTGTCTGGTATAGTGCAACAGCAGAACAATTTGCTG
1501  AGGGCTATTGAGGCGCAACAGCGTATGTTGCAACTCACAGTCTGGGGCAT
1551  CAAGCAGCTCCAGGCAAGAGTCCTGGCTGTGGAAAGATACCTAGGGGATC
1601  AACAGCTCCTGGGGATTTGGGGTTGCTCTGGAAAACTCATTTGCTGCACT
1651  GCTGTGCCTTGGAATGCTAGTTGGAGTAATAAATCTCTGGATAGGATTTG
1701  GAATAACATGACCTGGATGGAGTGGGAAAGAGAAATTGACAATTACACAA
1751  GCGAAATATACACCCTAATTGAAGAATCGCAGAACCAACAAGAAAAGAAT
1801  GAACAAGAATTATTGGAATTAGATAAATGGGCAAGTTTGTGGAATTGGTT
1851  TGACATAACAAAATGGCTGTGGTAT
```

*FIGURE 15B*

```
30    VEKLWVTVYY GVPVWKEATT TLFCASDAKA YDTEVHNVWA THACVPTDPN
80    PQEVVLENVT EHFNMWKNNM VEQMQEDIIS LWDQSLKPCV KLTPLCVTLN
130   CKDVNATNTT NDSEGTMERG EIKNCSFNIT TSIRDEVQKE YALFYKLDVV
180   XIDNNNTSYR LISCDTSVIT QACPKISFEP IPIHYCAPAG FAILKCNDKT
230   FNGKXPCKNV STXQCTHGIR PVVSTQLLLN GSLAEEEVVI RSDNFTNNAK
280   TIIVQLKESV EINCTRPNNN GAGDIRQAHC NISRAKWNDT LKQIVIKLRE
330   QFENKTIVFN HSSGGDPEIV MHSFNCGGEF FYCNSTQLFN STWNNNTEGS
380   NNTEGNTITL PCRIKQIINM WQEVGKAMYA PPIRGQIRCS SNITGLLLTR
430   DGGINENGTE IFRPGGGDMR DNWRSELYKY KVVKIEPLGV APTKCKRRVV
480   QREKRAVGIG AVFLGFLGAA GSTMGAASMT LTVQARLLLS GIVQQQNNLL
530   RAIEAQQRML QLTVWGIKQL QARVLAVERY LGDQQLLGIW GCSGKLICCT
580   AVPWNASWSN KSLDRIWNNM TWMEWEREID NYTSEIYTLI EESQNQQEKN
630   EQELLELDKW ASLWNWFDIT KWLWY
```

STABILIZED VIRAL ENVELOPE PROTEINS AND USES THEREOF

This application is a continuation-in-part of and claims the benefit of U.S. Provisional Application No. 60/141,168, filed Jun. 25, 1999, the contents of which are hereby incorporated by reference.

The invention disclosed herein was made with Government support under NIH Grant No. R01 Al 45463-01 from the Department of Health and Human Services. Accordingly, the government has certain rights in this invention.

Throughout this application, various publications are referenced. The disclosure of these publications is hereby incorporated by reference into this application to describe more fully the art to which this invention pertains.

BACKGROUND OF THE INVENTION

The human immunodeficiency virus (HIV) is the agent that causes AIDS, a lethal disease characterized by deterioration of the immune system. The initial phase of the HIV replicative cycle involves the attachment of the virus to susceptible host cells followed by fusion of viral and cellular membranes. These events are mediated by the exterior viral envelope glycoproteins, which are first synthesized as a fusion-incompetent precursor envelope glycoprotein (env) known as gp160. The gp160 glycoprotein is endoproteolytically processed to the mature envelope glycoproteins gp120 and gp41, which are noncovalently associated on the surface of the virus. The gp120 surface protein contains the high affinity binding site for human CD4, the primary receptor for HIV, as well as domains that interact with fusion coreceptors, such as the chemokine receptors CCRS and CXCR4. The gp41 protein spans the viral membrane and contains at its amino-terminus a sequence of amino acids important for the fusion of viral and cellular membranes. The HIV envelope glycoproteins assemble as noncovalent oligomers, almost certainly trimers, of gp120/gp41 on the virus surface. The detailed events of viral entry remain poorly understood but involve gp120 binding first CD4 then a fusogenic chemokine receptor, followed by gp41-mediated virus-cell fusion.

Because of their location on the virion surface and central role in mediating viral entry, the HIV envelope glycoproteins provide important targets for HIV vaccine development. Although most HIV-infected individuals mount a robust antibody (Ab) response to the envelope glycoproteins, most anti-gp120 and anti-gp41 Abs produced during natural infection bind weakly or not at all to virions and are thus functionally ineffective. These Abs are probably elicited and affinity matured against "viral debris" comprising gp120 monomers or improperly processed oligomers released from virions or infected cells. (Burton and Montefiori, AIDS, 11 [Suppl A]:587, 1997)

Several preventive HIV-1 subunit vaccines have been tested in Phase I and II clinical trials and a multivalent formulation is entering Phase III testing. These vaccines have contained either monomeric gp120 or unprocessed gp160 proteins. In addition, the vaccines mostly have been derived from viruses adapted to grow to high levels in immortalized T cell lines (TCLA viruses). These vaccines have consistently elicited Abs which neutralize the homologous strain of virus and some additional TCLA viruses. However, the Abs do not potently neutralize primary HIV-1 isolates (Mascola et al., J. Infec. Dis. 173:340, 1996). Compared with TCLA strains, the more clinically relevant primary isolates typically possess a different cellular tropism, show a different pattern of coreceptor usage, and have reduced sensitivity to neutralization by soluble CD4 and Abs. These differences primarily map to the viral envelope glycoproteins (Moore and Ho, AIDS, 9 [Suppl A]:S117–S136, 1995).

The Importance of Oligomerization in Envelope Glycoprotein Structure

There is a growing awareness that current-generation HIV subunit vaccines do not adequately present key neutralization epitopes as they appear on virions (Parren et al, Nat. Med. 3:366, 1997). There are several ways in which the native structure of virions affects the presentation of antibody epitopes. Firstly, much of the surface area of gp120 and gp41 is occluded by inter-subunit interactions within the trimer. Hence several regions of gp120, especially around the N- and C-termini, that are well exposed (and highly immunogenic) on the monomeric form of the protein, are completely inaccessible on the native trimer (Moore et al, J. Virol 68:469, 1994). This means that a subset of Abs raised to gp120 monomers are irrelevant, whether they arise during natural infection (because of the shedding of gp120 monomers from virions or infected cells) or after gp120 subunit vaccination. This provides yet another level of protection for the virus; the immune system is decoyed into making Abs to shed gp120 that are poorly reactive, and hence ineffective, with virions.

A second, more subtle problem is that the structure of key gp120 epitopes can be affected by oligomerization. A classic example is provided by the epitope for the broadly neutralizing human MAb IgG1b12 (Burton et al. Science 266:1024, 1994). This epitope overlaps the CD4-binding site on gp120 and is present on monomeric gp120. However, IgG1b12 reacts far better with native, oligomeric gp120 than might be predicted from its monomer reactivity, which accounts for its unusually potent neutralization activity (77,99–103). Thus the IgG1b12 epitope is oligomer-dependent, but not oligomer-specific. The converse situation is more common, unfortunately; many Abs that are strongly reactive with CD4-binding site-related epitopes on monomeric gp120, fail to react with the native trimer, and consequently do not neutralize the virus. In some undefined way, oligomerization of gp120 adversely affects the structures recognized by these Mabs. (Fouts et al., J Virol 71: 2779, 1997).

A third example of the problems caused by the native structure of the HIV-1 envelope glycoproteins is provided by gp41 MAbs. Only a single gp41 MAb (2F5) is known to have strong neutralizing activity against primary viruses (Trkola et al., J Virol, 69: 6609, 1995), and among those tested, 2F5 alone is thought to recognize an intact, gp120-gp41 complex (Sattentau et al, Virology 206: 713, 1995). All other gp41 MAbs that bind to virions or virus-infected cells probably react with fusion-incompetent gp41 structures from which gp120 has dissociated. Since the most stable form of gp41 is this post-fusion configuration (Weissenhorm et al, Nature, 387: 426, 1997), it can be supposed that most anti-gp41 Abs are raised (during natural infection or after gp160 vaccination) to an irrelevant gp41 structure that is not present on the pre-fusion form.

Despite these protective mechanisms, most HIV-1 isolates are potently neutralized by a limited subset of broadly reactive human monoclonal antibodies (MAbs), so induction of a relevant humoral immune response is not impossible. Mab IgG1b12, blocks gp120-CD4 binding; a second (2G12; Trkola et al. J Virol 70: 1100, 1996) acts mostly by steric hindrance of virus-cell attachment; and 2F5 acts by directly compromising the fusion reaction itself. Critical to understanding the neutralization capacity of these MAbs is the recognition that they react preferentially with the fusion-competent, oligomeric forms of the envelope glycoproteins, as found on the surfaces of virions and virus-infected cells. (Parren et al J. Virol 72: 3512, 1998). This distinguishes them from their less active peers. The limited number of MAbs that are oligomer-reactive explains why so few can neutralize primary viruses. Thus with rare exceptions, neutralizing anti-HIV Abs are capable of binding infectious virus while non-neutralizing Abs are not (Fouts et al AIDS Res Human Retrovir. 14: 591, 1998). Neutralizing Abs also have the potential to clear infectious virus through effector functions, such as complement-mediated virolysis.

Modifying the Antigenic Structure of the HIV Envelope Glycoproteins

HIV-1 has evolved sophisticated mechanisms to shield key neutralization sites from the humoral immune response, and in principle these mechanisms can be "disabled" in a vaccine. One example is the V3 loop, which for TCLA viruses in particular is an immunodominant epitope that directs the antibody response away from more broadly conserved neutralization epitopes. HIV-1 is also protected from humoral immunity by the extensive glycosylation of gp120. When glycosylation sites were deleted from the V1/V2 loops of SIV gp120, not only was a neutralization-sensitive virus created, but the immunogenicity of the mutant virus was increased so that a better immune response was raised to the wild-type virus (Reitter et al, Nat Med 4:679, 1998). Similarly, removing the V1/V2 loops from HIV-1 gp120 renders the conserved regions underneath more vulnerable to Abs (Cao et al, J. Virol. 71: 9808, 1997), although it is not yet known whether this will translate into improved immunogenicity.

Of note is that the deletion of the V1, V2 and V3 loops of the envelope glycoproteins of a TCLA virus did not improve the induction of neutralizing Abs in the context of a DNA vaccine (Lu et al, AIDS Res Human Retrovir 14:151, 1998). However, the instability of the gp120-gp41 interaction, perhaps exacerbated by variable loop deletions, may have influenced the outcome of this experiment. DNA plasmid, viral vector and other nucleic acid-based HIV vaccines may thus benefit from the gp120-gp41 stabilizations described in this invention. By increasing the time that the gp120-gp41 complex is presented to the immune system, stabilized envelope proteins expressed in vivo provide a means in principle to significantly improve upon the immune response elicited during natural infection.

Native and Non-native Oligomeric Forms of the HIV Envelope Glycoproteins

Current data suggest that on the HIV virion three gp120 moieties are non-covalently associated with three, underlying gp41 components in a meta-stable configuration whose fusion potential is triggered by interaction with cell surface receptors. This pre-fusion form may optimally present neutralization epitopes. We refer to this form of the envelope glycoproteins as native gp120-gp41. However, other oligomeric forms are possible, and it is important to define these (see FIG. 1).

Gp160: The full-length gp160 molecule often aggregates when expressed as a recombinant protein, at least in part because it contains the hydrophobic transmembrane domain. One such molecule is derived from a natural mutation that prevents the processing of the gp160 precursor to gp120/gp41 (VanCott et al J Virol 71: 4319, 1997). The gp160 precursor does not mediate virus-cell fusion and is a poor mimic of fusion-competent gp120/gp41. When evaluated in humans, recombinant gp160 molecules offered no advantages over gp120 monomers (Gorse et al., Vaccine 16: 493, 1998).

Uncleaved gp140 (gp140UNC): Stable "oligomers" have been made by eliminating the natural proteolytic site needed for conversion of the gp160 precursor protein into gp120 and gp41 (Berman et al, J Virol. 63: 3489, 1989; Earl et al Proc. Natl Acad Sci 87: 648, 1990). To express these constructs as soluble proteins, a stop codon is inserted within the env gene to truncate the protein immediately prior to the transmembrane-spanning segment of gp41. The protein lacks the transmembrane domain and the long, intracytoplasmic tail of gp41, but retains the regions important for virus entry and the induction of neutralizing Abs. The secreted protein contains full-length gp120 covalently linked through a peptide bond to the ectodomain of gp41. The protein migrates in SDS-PAGE as a single species with an apparent molecular mass of approximately 140 kilodaltons (kDa) under both reducing and nonreducing conditions. The protein forms higher molecular weight noncovalent oligomers, likely through interactions mediated by the gp41 moieties.

Several lines of evidence suggest that the uncleaved gp140 molecule does not adopt the same conformation as native gp120-gp41. These include observations described herein and from the finding that uncleaved gp120-gp41 complexes do not avidly bind fusion co-receptors (R. Doms, personal communication). Furthermore, a gp140 protein of this type was unable to efficiently select for neutralizing MAbs when used to pan a phage-display library, whereas virions were efficient (Parren et al, J Virol. 70:9046, 1996). We refer to the uncleaved gp120-gp41 ectodomain material as gp140UNC.

Cleavable but uncleaved gp140 (gp140NON): During biosynthesis, gp160 is cleaved into gp120 and gp41 by a cellular endoprotease of the furin family. Mammalian cells have a finite capacity to cleave gp120 from gp41, as we show below. Thus, when over-expressed, the envelope glycoproteins can saturate the endogenous furin enzymes and be secreted in precursor form. Since these molecules are potentially cleavable, we refer to them as gp140NON. Like gp140UNC, gp140NON migrates in SDS-PAGE with an apparent molecular mass of approximately 140 kDa under both reducing and nonreducing conditions. As shown below, gp140NON appears to possess the same non-native topology as gp140UNC.

Cleaved gp140 (gp140CUT): gp140CUT refers to full-length gp120 and ectodomain gp41 fully processed and capable of forming oligomers as found on virions. The noncovalent interactions between gp120 and gp41 are sufficiently long-lived for the virus to bind and initiate fusion with new target cells, a process which is likely completed within minutes during natural infection. The association has, however, to date proven too labile for the production of significant quantities of cleaved gp140s in near homogenous form.

Stabilization of Viral Envelope Glycoproteins

The metastable pre-fusion conformation of viral envelope proteins such as gp120/gp41 has evolved to be sufficiently stable so as to permit the continued spread of infection yet sufficiently labile to readily allow the conformational changes required for virus-cell fusion. For the HIV isolates examined thus far, the gp120-gp41 interaction has proven too unstable for preparative-scale production of gp140CUT as a secreted protein. Given the enormous genetic diversity of HIV, however, it is conceivable that viruses with superior env stability could be identified using screening methods such as those described herein. Alternatively, viruses with heightened stability could in principle be selected following successive exposure of virus to conditions known to destabilize the gp120-gp41 interaction. Such conditions might include elevated temperatures in the range of 37–60° C. and/or low concentrations of detergents or chaotropic agents. The envelope proteins from such viruses could be subcloned into the pPPI4 expression vector and analyzed for stability using our methods as well.

One could also adopt a semi-empirical, engineered approach to stabilizing viral envelope proteins. For example stable heterodimers have been successfully created by introducing complementary "knob" and "hole" mutations in the binding partners (Atwell et al., J. Mol. Biol. 4:26, 1997). Alternatively or in addition, one could introduce other favorable interactions, such as salt bridges, hydrogen bonds, or hydrophobic interactions. This approach is facilitated by increased understanding of the structures of the SU and TM proteins, and the results described herein contribute to this understanding.

As we demonstrate in this invention, SU-TM stabilization can also be achieved by means of one or more introduced disulfide bonds. Among mammalian retroviruses, only the lentiviruses such as HIV have non-covalent associations between the surface (SU) and transmembrane (TM) glycoproteins. In contrast, the type C and type D retroviruses all have an inter-subunit disulfide bond. The ectodomains of retroviral TM glycoproteins have a broadly common structure, one universal feature being the presence of a small, Cys—Cys bonded loop approximately central in the ectodomain. In the type C and D retroviral TM glycoproteins, an unpaired cysteine residue is found immediately C-terminal to this loop and is almost certainly used in forming the SU—TM disulfide bond. (Gallaher et al, AIDS Res Human Retrovir 11: 191, 1995; Schultz et al AIDS Res Human Retrovir, 8: 1585, 1992)

Although gp41 and other lentiviral TM glycoproteins lack the third cysteine, the structural homologies suggest that one could be inserted in the vicinity of the short central loop structure. Thus there is strong mutagenic evidence that the first and last conserved regions of gp120 (C1 and C5 domains) are probable contact sites for gp41.

The subject invention provides isolated nucleic acid molecules that encode mutant viral surface and transmembrane proteins in stabilized, antigenically authentic forms. This invention describes the design and synthesis of the stabilized viral proteins. Importantly, when appropriate methods are used to effect the stabilization, the viral proteins adopt conformations with desirable features. The subject invention further provides protein- or nucleic acid-based vaccines comprising mutant viral envelope proteins, antibodies isolated or identified using mutant viral envelope proteins, pharmaceutical compositions comprising these vaccines or antibodies, and methods of using these compositions to treat or prevent infections from viruses such as HIV. The invention describes applications of the mutant viral proteins to identify whether a compound is capable of inhibiting a virus, and compounds identified in this manner.

SUMMARY OF THE INVENTION

This invention provides an isolated nucleic acid which comprises a nucleotide segment having a sequence encoding a viral envelope protein comprising a viral surface protein and a corresponding viral transmembrane protein wherein the viral envelope protein contains one or more mutations in amino acid sequence that enhance the stability of the complex formed between the viral surface protein and the viral transmembrane protein.

This invention provides an isolated nucleic acid which comprises a nucleotide segment having a sequence encoding a mutant viral envelope protein which differs from the corresponding wild type viral envelope protein sequence in at least one amino acid which upon proteolysis yields a complex comprising a surface protein and a transmembrane protein which has enhanced stability relative to the corresponding complex obtained from the wild type envelope protein.

In one embodiment of the above the viral surface protein is HIV-1 gp120 or a modified form of gp120 which has modified immunogenicity relative to wild type gp120. In one embodiment, the transmembrane protein is HIV-1 gp41 or a modified form of gp41 which has modified immunogenicity relative to wild type gp41.

This invention provides a vaccine which comprises the above isolated nucleic acid. In one embodiment, the vaccine comprises a therapeutically effective amount of the nucleic acid. In another embodiment, the vaccine comprises a therapeutically effective amount of the protein encoded by the above nucleic acid. In another embodiment, the vaccine comprises a combination of the recombinant nucleic acid molecule and the mutant viral envelope protein.

This invention provides a method of treating a viral disease which comprises immunizing a virally infected subject with the above vaccines or a combination thereof, thereby treating the subject.

This invention provides a vaccine which comprises a prophylactically effective amount of the above isolated nucleic acid.

This invention provides a vaccine which comprises a prophylactically effective amount of the protein encoded by the above isolated nucleic acid.

This invention provides a method of reducing the likelihood of a subject becoming infected with a virus comprising administering the above vaccines or a combination thereof, thereby reducing the likelihood of the subject becoming infected with the virus.

This invention provides the above vaccine which comprises but is not limited to the following: a recombinant subunit protein, a DNA plasmid, an RNA molecule, a replicating viral vector, a non-replicating viral vector, or a combination thereof.

This invention provides a method of reducing the severity of a viral disease in a subject comprising administering the above vaccine or a combination thereof, prior to exposure of the subject to the virus, thereby reducing the severity of the viral disease in the subject upon subsequent exposure to the virus.

This invention provides a mutant viral envelope protein which differs from the corresponding wild type protein in at least one amino acid which upon proteolysis yields a complex comprising a surface protein and a transmembrane protein which has enhanced stability relative to the corresponding complex obtained from the wild type envelope protein.

This invention provides a complex comprising a viral surface protein and a viral transmembrane protein which has enhanced stability relative to the corresponding complex obtained from the wildtype envelope protein, yielded by the proteolysis of a mutant viral envelope protein with a sequence which differs from the corresponding wild type protein sequence in at least one amino acid.

This invention provides a mutant viral envelope protein which is encoded by the above nucleic acid molecule.

This invention provides a vaccine which comprises a therapeutically effective amount of the above protein or complex. This invention also provides a vaccine which comprises a prophylactically effective amount of the above protein or complex.

This invention provides a method of stimulating or enhancing in a subject production of antibodies which recognize the above protein or complex.

This invention provides a method of stimulating or enhancing in a subject the production of cytotoxic T lymphocytes which recognize the above protein.

This invention provides an antibody capable of specifically binding to the above mutant protein. This invention also provides an antibody which is capable of specifically binding to the above mutant protein or complex but not to the wild type protein or complex.

This invention provides an antibody, antibody chain or fragment thereof identified using the viral envelope protein encoded by the above recombinant nucleic acid molecule. The antibody may be of the IgM, IgA, IgE or IgG class or subclasses thereof. The above antibody fragment includes but is not limited to Fab, Fab', (Fab')2, Fv and single chain antibodies.

This invention provides an isolated antibody light chain of the above antibody, or fragment or oligomer thereof. This invention also provides an isolated antibody heavy chain of the above antibody, or fragment or oligomer thereof. This invention also provides one or more CDR regions of the above antibody. In one embodiment, the antibody is derivatized. In another embodiment, the antibody is a human antibody. The antibody includes but is not limited to monoclonal antibodies and polyclonal antibodies. In one embodiment, antibody is humanized.

This invention provides an isolated nucleic acid molecule encoding the above antibody.

This invention provides a method of reducing the likelihood of a virally exposed subject from becoming infected with the virus comprising administering the above antibody or the above isolated nucleic acid, thereby reducing the likelihood of the subject from becoming infected with the virus.

This invention provides a method of treating a subject infected with a virus comprising administering the above antibody or the above isolated nucleic acid, thereby treating the subject. In a preferred embodiment, the virus is HIV.

This invention provides an agent capable of binding the mutant viral envelope protein encoded by the above recombinant nucleic acid molecule. In one embodiment, the agent inhibits viral infection.

This invention provides a method for determining whether a compound is capable of inhibiting a viral infection comprising:

(A) contacting an appropriate concentration of the compound with the mutant viral envelope protein encoded by the recombinant nucleic acid of claim 1 under conditions permitting binding of the compound to said protein;

(B) contacting the resulting complex with a reporter molecule under conditions that permit binding of the reporter molecule to the mutant viral envelope protein;

(C) measuring the amount of bound reporter molecule; and (D) comparing the amount of bound reporter molecule in step (C) with the amount determined in the absence of the compound, a decrease in the amount indicating that the compound is capable of inhibiting infection by the virus, thereby determining whether a compound is capable of inhibiting a viral infection.

This invention provides a method for determining whether a compound is capable of inhibiting a viral infection which comprises:

(a) contacting an appropriate concentration of the compound with a host cell viral receptor or molecular mimic thereof under conditions that permit binding of the compound and receptor or receptor mimic;

(b) contacting the resulting complex with the mutant viral envelope protein encoded by the recombinant nucleic acid of claim 1 under conditions that permit binding of the envelope protein and receptor or receptor mimic in the absence of the compound;

(c) measuring the amount of binding of envelope protein to receptor or receptor mimic;

(d) comparing the amount of binding determined in step (c) with the amount determined in the absence of the compound, a decrease in the amount indicating that the compound is capable of inhibiting infection by the virus, thereby determining whether a compound is capable of inhibiting a viral infection.

This invention further provides a simple method for determining whether a subject has produced antibodies capable of blocking the infectivity of a virus.

This invention provides the above method wherein the compound was not previously known.

This invention provides a compound determined to be capable of inhibiting a viral infection by the above methods.

This invention provides a pharmaceutical composition comprising an amount of the compound effective to inhibit viral infection determined by the above methods to be capable of inhibiting viral infection and a pharmaceutically acceptable carrier. In one embodiment, wherein the viral infection is HIV-1 infection. In the preferred embodiment, the virus is HIV.

This invention provides a mutant viral envelope protein which differs from the corresponding wild type protein in at least one amino acid which yields a complex comprising a surface protein and a transmembrane protein which has enhanced stability relative to the corresponding complex obtained from the wild type envelope protein, wherein the surface protein and transmembrane protein are encoded by different nucleic acids.

This invention provides a complex comprising a viral surface protein and a viral transmembrane protein which has enhanced stability relative to the corresponding complex obtained from the wildtype envelope protein, yielded by the proteolysis of a mutant viral envelope protein with a sequence which differs from the corresponding wild type protein sequence in at least one amino acid, wherein the surface protein and transmembrane protein are encoded by different nucleic acids.

This invention provides an antibody which binds to the above protein or above complex but does not cross react with the individual monomeric surface protein or the individual monomeric transmembrane protein. This invention provides the above antibody capable of binding to the HIV-1 virus.

Figure 1:
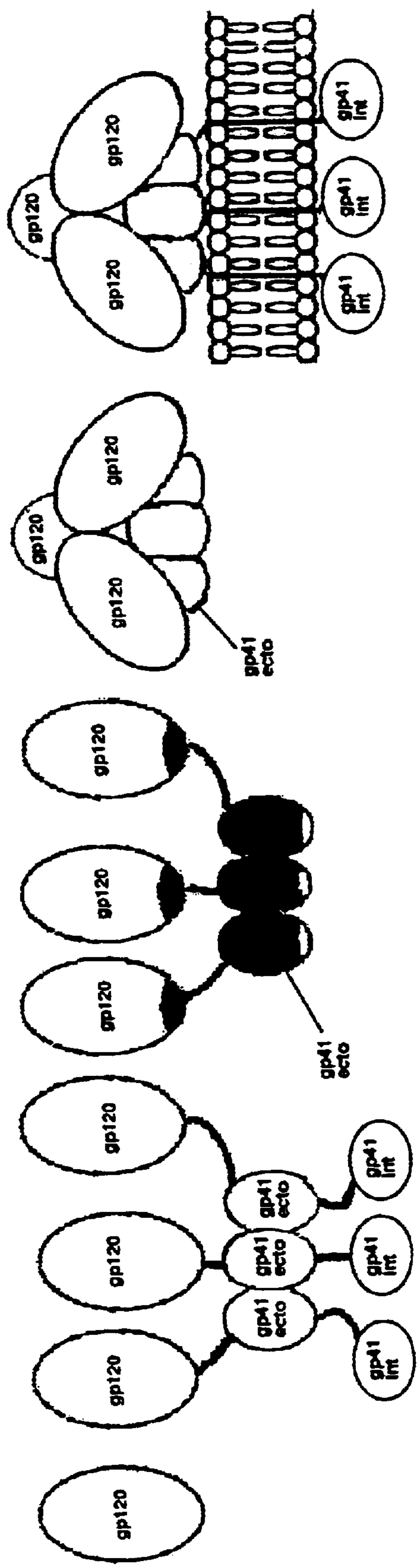
FIG. 1.

Different forms of the HIV-1 envelope glycoproteins

The cartoons depict: i) Monomeric gp120; ii) Full-length recombinant gp160 iii) Proteolytically unprocessed gp140 trimer with the peptide bond maintained between gp120 and gp41 (gp140UNC or gp140NON); iv) The SOS gp140 protein, a proteolytically processed gp140 stabilized by an intermolecular disulfide bond; v) Native, virion-associated gp120-gp41 trimer. The shading of the gp140UNC protein (iii) indicates the major antibody-accessible regions that are poorly, or not, exposed on the SOS gp140 protein or on the native gp120-gp41 trimer.

FIG. 2.

Co-transfection of furin increases the efficiency of cleavage of the peptide bond between gp120 and gp41

293T cells were transfected with DNA expressing HIV-1 JR-FL gp140WT or gp140UNC(gp120-gp41 cleavage-site mutant) proteins, in the presence or absence of a co-transfected furin-expressing plasmid. The 35S-labelled envelope glycoproteins secreted from the cells were immunoprecipitated with the anti-gp120 MAb 2G12, then analyzed by SDS-PAGE. Lane 1, gp140WT(gp140/gp120 doublet); Lane 2, gp140WT plus furin (gp120 only); Lane 3, gp140UNC (gp140 only); lane 4, gp140UNC plus furin (gp140 only). The approximate molecular weights, in kDa, of the major species are indicated on the left.

FIG. 3.

Positions of cysteine substitutions in JR-FL gp140

The various residues of the JR-FL gp140WT protein that have been mutated to cysteines in one or more mutants are indicated by closed arrows on the schematics of the gp120 and gp41ECTO subunits. The positions of the alanine-492 and threonine-596 residues that are both mutated to cysteine in the SOS gp140 protein are indicated by the larger, closed arrows. a)JR-FL gp120. b) JR-FL gp41. The open boxes at the C-terminus of gp120 and the N-terminus of gp41 indicate the regions that are mutated in the gp140UNC protein to eliminate the cleavage site between gp120 and gp41.

FIG. 4.

Immunoprecipitation analysis of selected double cysteine mutants of JR-FL gp140

The 35S-labelled envelope glycoproteins secreted from transfected 293T cells were immunoprecipitated with anti-gp120 and anti-gp41 MAbs, then analyzed by SDS-PAGE. The MAbs used were either 2G12 (anti-gp120 C3-V4 region) or F91 (anti-gp120 CD4 binding site region).

The positions of the two cysteine substitutions in each protein (one in gp120, the other in gp41ECTO) are noted above the lanes. The gp140WT protein is shown in lane 15. All proteins were expressed in the presence of co-transfected furin, except for the gp140WT protein.

FIG. 5.

The efficiency of intermolecular disulfide bond formation is dependent upon the positions of the cysteine substitutions The 35S-labelled envelope glycoproteins secreted from 293T cells co-transfected with furin and the various gp140 mutants were immunoprecipitated with the anti-gp120 MAb 2G12, then analyzed by SDS-PAGE. For each mutant, the intensities of the 140 kDa and 120 kDa bands were determined by densitometry and the gp140/gp140+gp120 ratio was calculated and recorded. The extent of shading is proportional to the magnitude of the gp140/gp140+gp120 ratio. The positions of the amino acid substitutions in gp41 and the C1 and C5 domains of gp120 are recorded along the top and down the sides, respectively. N.D.=Not done.

FIG. 6.

Confirmation that an intermolecular gp120-gp41 bond forms in the SOS gp140 protein 293T cells were transfected with plasmids expressing gp140 proteins and, when indicated, a furin-expressing plasmid. The secreted, 35S-labelled glycoproteins were immunoprecipitated with the indicated MAbs and analyzed by SDS-PAGE under reducing (+DTT) or nonreducing conditions.

A. Radioimmunoprecipitations with 2G12 of the SOS gp140, gp140WT and gp140UNC proteins. Immunoprecipitated proteins were resolved by SDS-PAGE under reducing (Lanes 4–6) or non-reducing (Lanes 1–3) conditions.

B. Radioimmunoprecipitations with 2G12 of the SOS gp140 protein and gp140 proteins containing the corresponding single-cysteine mutations. 140 kDa protein bands are not observed for either the A492C or the T596C single-cysteine mutant gp140 proteins.

C. Radioimmunoprecipitations with 2G12 of the SOS gp140 proteins produced in the presence or absence of co-transfected furin. Immunoprecipitated proteins were resolved by SDS-PAGE under reducing (Lanes 3–4) or non-reducing (Lanes 1–2) conditions. DTT is shown to reduce the 140 kDa SOS protein band produced in the presence but not the absence of exogenous furin.

FIG. 7.

Analysis of cysteine mutants of JR-FL gp140

The 35S-labelled envelope glycoproteins secreted from transfected 293T cells were immunoprecipitated with the anti-gp120 MAb 2G12, then analyzed by SDS-PAGE. All gp140s were expressed in the presence of co-transfected furin. Lanes 1–8, gp140s containing the indicated double cysteine mutations. Lanes 9–11, gp140 proteins containing the A492C/T596C double cysteine substitutions together with the indicated lysine to alanine substitutions at residue 491 (lane 9), residue 493 (lane 10) or at both residues 491 and 493 (lane 11). Lanes 12–14, gp140 proteins containing quadruple cysteine substitutions.

FIG. 8.

Comparison of the antigenic structures of the SOS gp140, W44C/T596C gp140 mutant. gp140UNC and gp140WT proteins The 35S-labelled envelope glycoproteins secreted from transfected 293T cells were immunoprecipitated with the indicated anti-gp120 Mabs and anti-gp41 MAbs, then analyzed by SDS-PAGE. Mutant but not wild type gp140s were expressed in the presence of cotransfected furin.

A. Anti-gp120 immunoglobulins that neutralize HIV-$1_{JR-FL}$.

B. Non-neutralizing antibodies to the C1, C4 and C5 regions of gp120.

C. Antibodies to CD4-induced epitopes were examined alone and in combination with sCD4.

D. Neutralizing (2F5) and non-neutralizing (7B2, 2.2B and 25C2) anti-gp41 antibodies and MAb 2G12.

E. Radioimmunoprecipitations of gp140WT (odd numbered lanes) and gp140UNC (even numbered lanes).

FIG. 9

Preparation of disulfide bond-stabilized gp140 proteins from various HIV-1 isolates 293T cells were transfected with plasmids expressing wild type or mutant gp140s in the presence or absence of exogenous furin as indicated. 35S-labeled supernatants were prepared and analyzed by radioimmunoprecipitation with MAb 2G12 as described above. Lane 1: SOS gp140 protein. Lane 2: gp140WT plus furin. Lane 3: gp140WT without furin. (A)HIV-1 DH123. (B)HIV-1 HxB2

FIG. 10

Amino acid sequences of the glycoproteins with various deletions in the variable regions. The deleted wild-type sequences are shown in the white shade and include the following: ΔV1: D132-K152; ΔV2: F156-I191; ΔV1V2': D132-K152 and F156-I191; ΔV1V2*: V126-S192; ΔV3: N296-Q324

FIG. 11

Formation of an intersubunit cysteine bridge in envelope proteins with deletions in variable loop regions. a) The ΔV1V2*V3 protein and the ΔV1V2*V3 N357Q N398Q protein with two cysteines at positions 492 and 596 (indicated with CC) were precipitated with 2G12 and F91 (lanes 3 & 7 and 4 & 8, respectively). The appropriate controls without cysteine mutations are shown in lanes 1, 2, 5 & 6. The wild-type protein without extra cysteines is shown in lanes 9 and 10. All the proteins were cleaved by furin, except for the wild-type protein of lane 10. The approximate sizes in kDa are given on the right. b) Various loop deleted proteins with two cysteines at positions 492 and 596 (CC) were precipitated with 2G12 (lanes 3, 5, 7, 9, 11 & 13). Proteins with the same deletions without extra cysteines are given in the adjacent lanes. These control proteins were not cleaved by furin. The full-length SOS gp140 protein is included as a control in lane 1.

FIG. 12

Antigenic characterization of the A492C/T596C mutant in combination with deletions in the variable loops. All mutants were expressed in the presence of exogeneous furin. The abs used in RIPAs are indicated on top. a) The A492C/T596C ΔV1V2* mutant and b) the A492C/T596C ΔV3 mutant.

FIG. 13

Nucleotide (A) (SEQ ID NO:12) and amino acid (B) (SEQ ID NO:13) sequences for HIV-$1_{JR-FL}$ SOS gp140. The amino acid numbering system corresponds to that for wild-type JR-FL (Genbank Accession #U63632). The cysteine mutations are indicated in underlined bold type face. p Nucleotide (A) and amino acid (B) sequences for HIV-$1_{JR-FL}$ SOS gp140. The amino acid numbering system corresponds to that for wild-type JR-FL (Genbank Accession #U63632). The cysteine mutations are indicated in underlined bold type face.

FIG. 14

Nucleotide (A) (SEQ ID NO:14) and amino acid (B) (SEQ ID NO:15) sequences for HIV-$1_{JR-FL}$ ΔV1V2* SOS gp140. The amino acid numbering system corresponds to that for wild-type JR-FL (Genbank Accession #U63632). The cysteine mutations are indicated in underlined bold type face.

FIG. 15

Nucleotide (A)(SEQ ID NO:16) and amino acid (B) (SEQ ID NO:17) sequences for HIV-$1_{JR-FL}$ ΔV3 SOS gp140. The amino acid numbering system corresponds to that for wild-type JR-FL (Genbank Accession #U63632). The cysteine mutations are indicated in underlined bold type face.

DETAILED DESCRIPTION OF THE INVENTION

This invention provides an isolated nucleic acid which comprises a nucleotide segment having a sequence encoding a viral envelope protein comprising a viral surface protein and a corresponding viral transmembrane protein wherein the viral envelope protein contains one or more mutations in amino acid sequence that enhance the stability of the complex formed between the viral surface protein and transmembrane protein.

This invention provides an isolated nucleic acid which comprises a nucleotide segment having a sequence encoding a mutant viral envelope protein which differs from the corresponding wild type viral envelope protein sequence in at least one amino acid which upon proteolysis yields a complex comprising a surface protein and a transmembrane protein which has enhanced stability relative to the corresponding complex obtained from the wild type envelope protein.

As used herein, "enhance the stability" means make more long-lived or resistant to dissociation. The interaction may be stabilized by the introduction of disulfide bonds, salt bridges, hydrogen bonds, hydrophobic interactions, favorable van der Waals contacts, a linker peptide or a combination thereof. The stabilizing interactions may be introduced by recombinant methods. Alternatively or in combination, stabilized viral envelope proteins may be obtained by selection methods such as exposing a virus to conditions known to destabilize the interaction between the surface and transmembrane envelope proteins, and then selecting for resistant viruses. This process may be repeated one or more times until one obtains viral envelope proteins with the desired stability. Alternatively, one may screen isolates for naturally occurring mutations that enhance the stability of the interaction between the surface and transmembrane proteins, relative to the stability observed for prototypic wild type viral envelope proteins.

The invention does not encompass known viral proteins wherein the endoproteolytic processing of the precursor envelope protein to separate surface and transmembrane proteins is prevented by expressing the protein in the absence of sufficient quantities of the endoprotease or by mutating the endoproteolytic cleavage site in the absence of additional mutations, such as the addition of a linker peptide. In such known viral envelope proteins, the viral surface and transmembrane proteins are physically joined by a covalent bond but are not known to form a complex, as illustrated in FIG. 1.

One embodiment of the above virus is a lentivirus. In one embodiment, the virus is the simian immunodeficiency virus. Another embodiment of the above virus is the human immunodeficiency virus (HIV). The virus may be either of the two known types of HIV (HIV-1 or HIV-2). The HIV-1 virus may represent any of the known major subtypes (Clades A, B, C, D E, F, G and H) or outlying subtype (Group 0). Additional types, subtypes or classes of HIV may be discovered and used in this invention. In one embodiment, the human immunodeficiency virus is a primary isolate. In one embodiment, the human immunodeficiency virus is HIV-$1_{JR-FL}$. In another embodiment the human immunodeficiency virus is HIV-$1_{DH123}$. In another embodiment the human immunodeficiency virus is HIV-$1_{Gun-1}$. In another embodiment the human immunodeficiency virus is HIV-$1_{89.6}$. In another embodiment the human immunodeficiency virus is HIV-$1_{HXB2}$.

HIV-$1_{JR-FL}$ is a strain that was originally isolated from the brain tissue of an AIDS patient taken at autopsy and co-cultured with lectin-activated normal human PBMCs (O'Brien et al, Nature, 348: 69, 1990) HIV-$1_{JR-FL}$ is known to utilize CCR5 as a fusion coreceptor and has the ability to replicate in phytohemagglutinin (PHA)-stimulated PBMCs and blood-derived macrophages but does not replicate efficiently in most immortalized T cell lines.

HIV-$1_{DH123}$ is a clone of a virus originally isolated from the peripheral mononuclear cells (PBMCs) of a pateint with AIDS (Shibata et al., J. Virol 69:4453, 1995). HIV-$1_{DH123}$ is known to utilize both CCR5 and CXCR4 as fusion coreceptors and has the ability to replicate in PHA-stimulated PBMCS, blood-derived macrophages and immortalized T cell lines.

HIV-$1_{Gun\text{-}1}$ is a cloned virus originally isolated from the peripheral blood mononuclear cells of a hemophilia B patient with AIDS (Takeuchi et al., Jpn J Cancer Res 78:11 1987). HIV-$1_{Gun\text{-}1}$ is known to utilize both CCR5 and CXCR4 as fusion coreceptors and has the ability to replicate in PHA-stimulated PBMCs, blood-derived macrophages and immortalized T cell lines.

HIV-$1_{89.6}$ is a cloned virus originally isolated from a patient with AIDS (Collman et al, J. Virol. 66: 7517, 1992). HIV-$1_{89.6}$ is known to utilize both CCR5 and CXCR4 as fusion coreceptors and has the ability to replicate in PHA-stimulated PBMCs, blood-derived macrophages and immortalized T cell lines.

HIV-$1_{HXB2}$ is a TCLA virus that is known to utilize CXCR4 as a fusion coreceptor and has the ability to replicate in PHA-stimulated PBMCs and immortalized T cell lines but not blood derived macrophages.

Although the above strains are used herein to generate the mutant viral envelope proteins of the subject invention, other HIV-1 strains could be substituted in their place as is well known to those skilled in the art.

One embodiment of the above viral surface protein is gp120 or a modified form of gp120 which has modified immunogenicity relative to wild type gp120. In one embodiment, the modified gp120 molecule is characterized by the absence of one or more variable loops present in wild type gp120. In one embodiment, the variable loop comprises V1, V2, or V3. In one embodiment, the modified gp120 molecule is characterized by the absence or presence of one or more canonical glycosylation sites not present in wild type gp120. In one embodiment, one or more canonical glycosylation sites are absent from the V1V2 region of the gp120 molecule.

In one embodiment, the transmembrane protein is gp41 or a modified form of gp41 which has modified immunogenicity relative to wildtype gp41. In one embodiment, the transmembrane protein is full-length gp41. In another embodiment, the transmembrane protein contains the ectodomain and membrane anchoring sequence of gp41 but lacks a portion or all of the gp41 cytoplasmic sequences. In one embodiment, the transmembrane protein is the gp41 ectodomain. In one embodiment, the transmembrane protein is modified by deletion or insertion of one or more canonical glycosylation sites.

One embodiment of the above viral surface protein is gp120 or a derivative thereof. In one embodiment, the gp120 molecule has been modified by the deletion or truncation of one or more variable loop sequences. The variable loop sequences include but are not limited to V1, V2, V3 or a combination thereof. In another embodiment, the gp120 molecule has been modified by the deletion or insertion of one or more canonical glycosylation sites. The region of gp120 from which the canonical glycosylation sites are deleted includes but is not limited to the V1V2 region of the gp120 molecule.

Figure 10:
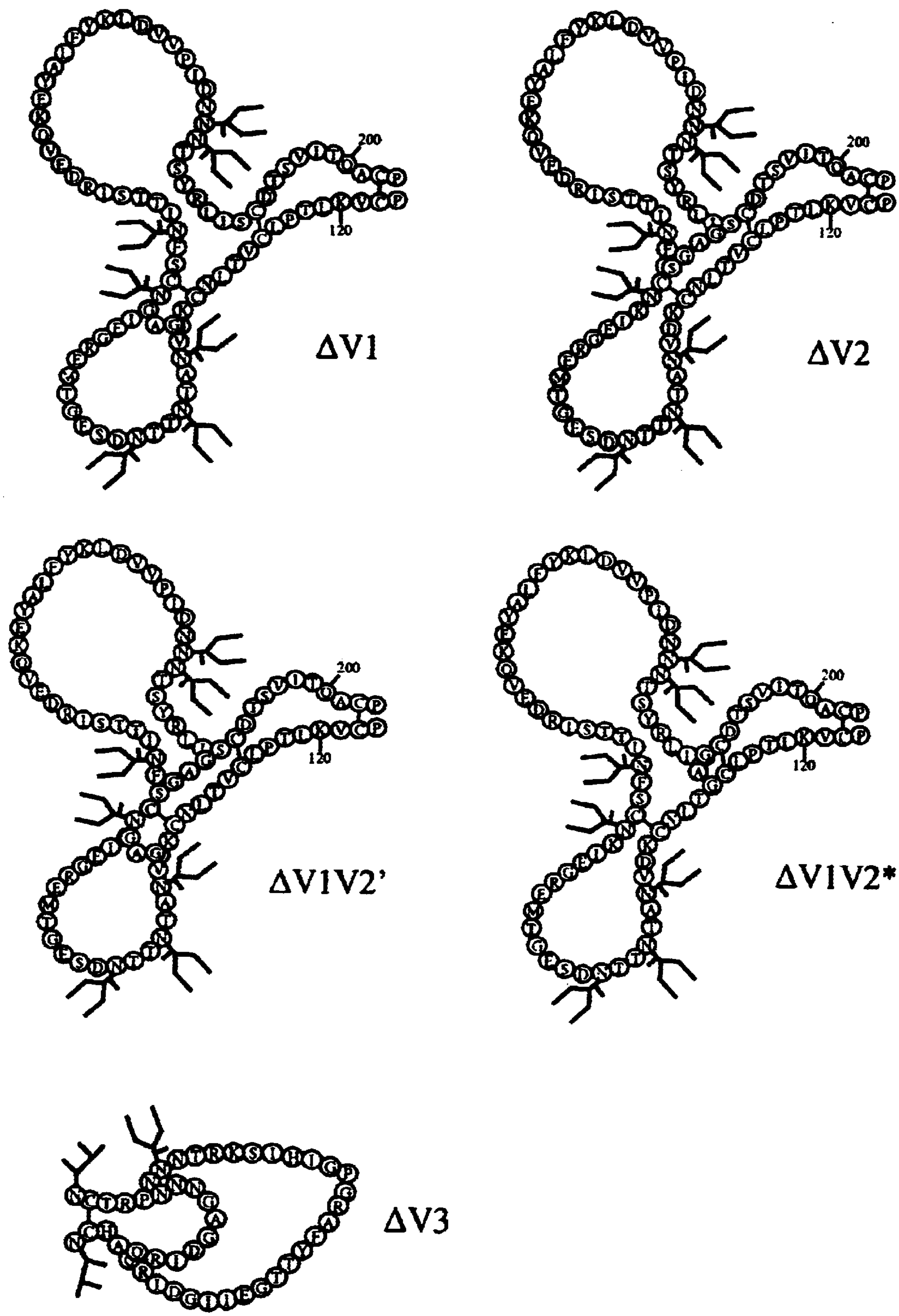

The V1, V2 and V3 variable loop sequences for HIV-$1_{JR\text{-}FL}$ are illustrated in FIG. 10. The amino acid sequences in these variable loops will vary for other HIV isolates but will be located in homologous regions of the gp120 envelope glycoprotein.

As used herein, "canonical glycosylation site" includes but is not limited to an Asn-X-Ser or Asn-X-Thr sequence of amino acids that defines a site for N-linkage of a carbohydrate. In addition, Ser or Thr residues not present in such sequences to which a carbohydrate can be linked through an O-linkage are "canonical glycosylation sites." In the later case of a "canonical glycosylation site," a mutation of the Ser and Thr residue to an amino acid other than a serine or threonine will remove the site of O-linked glycosylation.

When used in the context of gp41, "derivatives" include but are not limited to the gp41 ectodomain, gp41 modified by deletion or insertion of one or more glycosylation sites, gp41 modified so as to eliminate or mask the well-known imunodominant epitope, a gp41 fusion protein, and gp41 labeled with an affinity ligand or other detectable marker.

As used herein, "ectodomain" means the extracellular region or portion thereof exclusive of the transmembrane spanning and cytoplasmic regions.

In one embodiment, the stabilization of the mutant viral envelope protein is achieved by the introduction of one or more cysteine-cysteine bonds between the surface and transmembrane proteins.

In one embodiment, one or more amino acids which are adjacent to or which contain an atom within 5 Ångstroms of an introduced cysteine are mutated to a noncysteine residue.

As used herein, "adjacent to" means immediately preceding or following in the primary sequence of the protein.

As used herein, "mutated" means that which is different from the wild-type.

As used herein, "noncysteine residue" means an amino acid other than cysteine.

In one embodiment, one or more cysteines in gp120 or modified form of gp120 are disulfide linked to one or more cysteines in gp41 or modified form of gp41.

In one embodiment, a cysteine in the C5 region of gp120 or modified form of gp120 is disulfide linked to a cysteine in the ectodomain of gp41 or modified form. In one embodiment, the disulfide bond is formed between a cysteine introduced by an A492C mutation in gp120 or modified form of gp120 and an T596C mutation in gp41 or modified form of gp41.

As used herein, "C5 region" means the fifth conserved sequence of amino acids in the gp120 glycoprotein. The C5 region includes the carboxy-terminal amino acids. In HIV-$1_{JR\text{-}FL}$ gp120, the unmodified C5 region consists of the amino acids GGGDMRDNWRSELYKYKVVK-IEPLGVAPTKAKRRVVQRE (SEQ ID NO:1). Amino acid residues 462–500 of the sequence set forth in FIG. 3A have this sequence. In other HIV isolates, the C5 region will comprise a homologous carboxy-terminal sequence of amino acids of similar length.

As used herein, "A492C mutation" refers to a point mutation of amino acid 492 in HIV-$1_{JR\text{-}FL}$ gp120 from alanine to cysteine. Because of the sequence variability of HIV, this amino acid will not be at position 492 in all other HIV isolates. For example, in HIV-$1_{NL4\text{-}3}$ the corresponding amino acid is A499 (Genbank Accesion #AAA44992). It may also be a homologous amino acid other than alanine or cysteine. This invention encompasses cysteine mutations in such amino acids, which can be readily identified in other HIV isolates by those skilled in the art.

As used herein, "T596C mutation" refers to a point mutation of amino acid 596 in HIV-$1_{JR\text{-}FL}$ gp41 from threonine to cysteine.

Because of the sequence variability of HIV, this amino acid will not be at position 596 in all other HIV isolates. For example, in HIV-$1_{NL4\text{-}3}$ the corresponding amino acid is T603 (Genbank Accesion #AAA44992). It may also be a homologous amino acid other than threonine or cysteine. This invention encompasses cysteine mutations in such amino acids, which can be readily identified in other HIV isolates by those skilled in the art.

In another embodiment, a cysteine in the C1 region of gp120 is disulfide linked to a cysteine in the ectodomain of gp41.

As used herein, "C1 region" means the first conserved sequence of amino acids in the mature gp120 glycoprotein. The C1 region includes the amino-terminal amino acids. In $HIV_{JR\text{-}FL}$, the C1 region consists of the amino acids VEKLWVTVYYGVPVWKEATTTLFCASDAKAYDTEVHNVWATHACVPTDPN PQEVVLENVTEHFNMWKNNMVEQMQEDIISLWDQSLKPCVKLTPLCVTLN (SEQ ID NO:2). Amino acid resides 30–130 of the sequence set forth in FIG. 3A have this sequence. In other HIV isolates, the C1 region will comprise a homologous amino-terminal sequence of amino acids of similar length. W44C and P600C mutations are as defined above for A492 and T596 mutations. Because of the sequence variability of HIV, W44 and P600 will not be at positions 44 and 600 in all HIV isolates. In other HIV isolates, homologous, non-cysteine amino acids may also be present in the place of the tryptophan and proline. This invention encompasses cysteine mutations in such amino acids, which can be readily identified in other HIV isolates by those skilled in the art.

The above isolated nucleic acid includes but is not limited to cDNA, genomic DNA, and RNA One skilled in the art would know how to make the nucleic acid which encode mutant viral envelope proteins wherein the interaction between the viral surface and transmembrane proteins has been stabilized. Furthermore, one skilled in the art would know how to use these recombinant nucleic acid molecules to obtain the proteins encoded thereby, and practice the therapeutic and prophylactic methods of using same, as described herein for the recombinant nucleic acid molecule which encode mutant viral envelope proteins.

The invention provides a replicable vector comprising the above nucleic acid. This invention also provides a plasmid, cosmid, phage or YAC containing the above nucleic acid molecule. In one embodiment, the plasmid is designated PPI4. The invention is not limited to the PPI4 plasmid and may include other plasmids known to those skilled in the art.

In accordance with the invention, numerous vector systems for expression of the mutant glycoprotein may be employed. For example, one class of vectors utilizes DNA elements which are derived from animal viruses such as bovine papilloma virus, polyoma virus, adenovirus, vaccinia virus, baculovirus, retroviruses (RSV, MMTV or MOMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by (Okayama and Berg, Mol Cell Biol 3:280, 1983).

The vectors used in the subject invention are designed to express high levels of mutant viral envelope proteins in cultured eukaryotic cells as well as efficiently secrete these proteins into the culture medium. The targeting of the mutant envelope glycoproteins into the culture medium is accomplished by fusing in-frame to the mature N-terminus of the mutant envelope glycoprotein a suitable signal sequence such as that derived from the genomic open reading frame of the tissue plasminogen activator (tPA).

The mutant envelope protein may be produced by a) transfecting a mammalian cell with an expression vector for producing mutant envelope glycoprotein; b) culturing the resulting transfected mammalian cell under conditions such that mutant envelope protein is produced; and c) recovering the mutant envelope protein so produced.

Once the expression vector or DNA sequence containing the constructs has been prepared for expression, the expression vectors may be transfected or introduced into an appropriate mammalian cell host. Various techniques may be employed to achieve this, such as, for example, protoplast fusion, calcium phosphate precipitation, electroporation, retroviral transduction, or other conventional techniques. In the case of protoplast fusion, the cells are grown in media and screened for the appropriate activity. Expression of the gene encoding a mutant envelope protein results in production of the mutant protein.

Methods and conditions for culturing the resulting transfected cells and for recovering the mutant envelope protein so produced are well known to those skilled in the art, and may be varied or optimized depending upon the specific expression vector and mammalian host cell employed.

In accordance with the claimed invention, the preferred host cells for expressing the mutant envelope protein of this invention are mammalian cell lines. Mammalian cell lines include, for example, monkey kidney CV1 line transformed by SV40 (COS-7); human embryonic kidney line 293; baby hamster kidney cells (BHK); Chinese hamster ovary-cells-DHFR+(CHO); Chinese hamster ovary-cells DHFR− (DXB11); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127); and myeloma cell lines.

Other eukaryotic expression systems utilizing non-mammalian vector/cell line combinations can be used to produce the mutant envelope proteins. These include, but are not limited to, baculovirus vector/insect cell expression systems and yeast shuttle vector/yeast cell expression systems.

Methods and conditions for purifying mutant envelope proteins from the culture media are provided in the invention, but it should be recognized that these procedures can be varied or optimized as is well known to those skilled in the art.

This invention provides a host cell containing the above vector. In one embodiment, the cell is a eukaryotic cell. In another embodiment, the cell is a bacterial cell.

This invention provides a vaccine which comprises the above isolated nucleic acid. In one embodiment, the vaccine comprises a therapeutically effective amount of the nucleic acid. In another embodiment, the vaccine comprises a therapeutically effective amount of the protein encoded by the above nucleic acid. In another embodiment, the vaccine comprises a combination of the recombinant nucleic acid molecule and the mutant viral envelope protein.

Numerous adjuvants have been developed to enhance the immunogenicity of protein and/or nucleic acid vaccines. As used herein, adjuvants suitable for use with protein-based vaccines include, but are not limited to, alum, Freund's incomplete adjuvant (FIA), Saponin, Quil A, QS21, Ribi Detox, Monophosphoryl lipid A (MPL), and nonionic block copolymers such as L-121 (Pluronic; Syntex SAF). In a preferred embodiment, the adjuvant is alum, especially in the form of a thixotropic, viscous, and homogenous aluminum hydroxide gel. The vaccine of the subject invention may be administered as an oil in water emulsion. Methods of combining adjuvants with antigens are well known to those skilled in the art.

The adjuvant may be in particulate form. The antigen may be incorporated into biodegradable particles composed of poly-lactide-co-glycolide (PLG) or similar polymeric material. Such biodegradable particles are known to provide sustained release of the immunogen and thereby stimulate long-lasting immune responses to the immunogen. Other particulate adjuvants include but are not limited to a micellular mixture of Quil A and cholesterol known as immunostimulating complexes (ISCOMs) and aluminum or iron oxide beads. Methods for combining antigens and particulate adjuvants are well known to those skilled in the art. It is also known to those skilled in the art that cytotoxic T lymphocyte and other cellular immune responses are elicited when protein-based immunogens are formulated and administered with appropriate adjuvants, such as ISCOMs and micron-sized polymeric or metal oxide particles.

As used herein, suitable adjuvants for nucleic acid based vaccines include, but are not limited to, Quil A, interleukin-12 delivered in purified protein or nucleic acid form, short bacterial immunostimulatory nucleotide sequence such as CpG containing motifs, interleukin-2/Ig fusion proteins delivered in purified protein or nucleic acid form, oil in water micro-emulsions such as MF59, polymeric microparticles, cationic liposomes, monophosphoryl lipid A (MPL), immunomodulators such as Ubenimex, and genetically detoxified toxins such as *E. coli* heat labile toxin and cholera toxin from Vibrio. Such adjuvants and methods of combining adjuvants with antigens are well known to those skilled in the art.

A "therapeutically effective amount" of the mutant envelope protein may be determined according to methods known to those skilled in the art.

As used herein, "therapeutically effective amount" refers to a dose and dosing schedule sufficient to slow, stop or reverse the progression of a viral disorder. In a preferred embodiment, the virus is HIV.

This invention provides a method of treating a viral disease which comprises immunizing a virally infected subject with the above vaccines or a combination thereof, thereby treating the subject.

As used herein, "treating" means either slowing, stopping or reversing the progression of a viral disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with the virus.

As used herein, "immunizing" means administering a primary dose of the vaccine to a subject, followed after a suitable period of time by one or more subsequent administrations of the vaccine, so as to generate in the subject an immune response against the vaccine. A suitable period of time between administrations of the vaccine may readily be determined by one skilled in the art, and is usually on the order of several weeks to months.

Depending on the nature of the vaccine and size of the subject, the dose of the vaccine can range from about 1 $\mu$g to about 10 mg. In the preferred embodiment, the dose is about 300 $\mu$g.

As used herein, "virally infected" means the introduction of viral genetic information into a target cell, such as by fusion of the target cell membrane with the virus or infected cell. The target may be a bodily cell of a subject. In the preferred embodiment, the target cell is a bodily cell from a human subject.

As used herein, "subject" means any animal or artificially modified animal capable of becoming infected with the virus. Artificially modified animals include, but are not limited to, SCID mice with human immune systems. The animals include but are not limited to mice, rats, dogs, guinea pigs, ferrets, rabbits, and primates. In the preferred embodiment, the subject is a human.

This invention provides a vaccine which comprises a prophylactically effective amount of the above isolated nucleic acid.

This invention provides a vaccine which comprises a prophylactically effective amount of the protein encoded by the above isolated nucleic acid.

A prophylactically effective amount of the vaccine may be determined according to methods well known to those skilled in the art.

As used herein "prophylactically effective amount" refers to a dose and dosing schedule sufficient to reduce the likelihood of a subject becoming infected or to lessen the severity of the disease in subjects who do become infected.

This invention provides a method of reducing the likelihood of a subject becoming infected with a virus comprising administering the above vaccines or a combination thereof, thereby reducing the likelihood of the subject becoming infected with the virus.

As used herein, "the subject becoming infected with a virus" means the invasion of the subject's own cells by the virus.

As used herein, "reducing the likelihood of a subject's becoming infected with a virus" means reducing the likelihood of the subject's becoming infected with the virus by at least two-fold. For example, if a subject has a 1% chance of becoming infected with the virus, a two-fold reduction in the likelihood of the subject's becoming infected with the virus would result in the subject's having a 0.5% chance of becoming infected with the virus. In the preferred embodiment of this invention, reducing the likelihood of the subject's becoming infected with the virus means reducing the likelihood of the subject's becoming infected with the virus by at least ten-fold.

As used herein "administering" may be effected or performed using any of the methods known to one skilled in the art. The methods may comprise intravenous, intramuscular, oral, intranasal, transdermal or subcutaneous means.

This invention provides the above vaccine which comprises but is not limited to the following: a recombinant subunit protein, a DNA plasmid, an RNA molecule, a replicating viral vector, a non-replicating viral vector, or a combination thereof.

This invention provides a method of reducing the severity of a viral disease in a subject comprising administering the above vaccine or a combination thereof, prior to exposure of the subject to the virus, thereby reducing the severity of the viral disease in the subject upon subsequent exposure to the virus. In the preferred embodiment, the virus is HIV.

As used herein "reducing the severity of a viral disease in a subject" means slowing the progression of and/or lessening the symptoms of the viral disease. It also means decreasing the potential of the subject to transmit the virus to an uninfected subject.

As used herein, "exposure to the virus" means contact with the virus such that infection could result.

As used herein, "subsequent exposure" means an exposure after one or more immunizations.

This invention provides a mutant viral envelope protein which differs from the corresponding wild type protein in at least one amino acid which upon proteolysis yields a complex comprising a surface protein and a transmembrane protein which has enhanced stability relative to the corresponding complex obtained from the wild type envelope protein.

This invention provides a complex comprising a viral surface protein and a viral transmembrane protein which has enhanced stability relative to the corresponding complex obtained from the wildtype envelope protein, yielded by the proteolysis of a mutant viral envelope protein with a sequence which differs from the corresponding wild type protein sequence in at least one amino acid.

This invention provides a viral envelope protein comprising a viral surface protein and a corresponding viral transmembrane protein wherein the viral envelope protein contains one or more mutations in amino acid sequence that enhance the stability of the complex formed between the viral surface protein and transmembrane protein.

This invention provides a complex comprising a viral surface protein and a corresponding viral transmembrane protein of a viral envelope protein wherein the viral envelope protein contains one or more mutations in amino acid sequence that enhance the stability of the complex formed between the viral surface protein and transmembrane protein.

This invention provides a mutant viral envelope protein which is encoded by the above nucleic acid molecule.

In one embodiment, the mutant viral envelope protein is linked to at least one other protein or protein fragment to form a fusion protein.

This invention provides a virus-like particle which comprises the transmembrane protein and surface protein complex of the subject invention. In one embodiment, the virus-like particle comprises an immunodeficiency virus structural protein. In one embodiment, the structural protein is the gag protein.

As used herein, "virus-like particles" or VLPs are particle which are non-infectious in any host, nonreplicating in any host, which do not contain all of the protein components of live virus particles. As used herein, VLPs of the subject invention contain the disulfide-stabilized complex of the subject invention and a structural protein, such as HIV-1 gag, needed to form membrane-enveloped virus-like particles.

Advantages of VLPs include (1) their particulate and multivalent nature, which is immunostimulatory, and (2) their ability to present the disulfide-stabilized envelope glycoproteins in a near-native, membrane-associated form.

VLPs are produced by co-expressing the viral proteins (e.g., HIV-1 gp120/gp41 and gag) in the same cell. This can be achieved by any of several means of heterologous gene expression that are well-known to those skilled in the art, such as transfection of appropriate expression vector(s) encoding the viral proteins, infection of cells with one or more recombinant viruses (e.g., vaccinia) that encode the VLP proteins, or retroviral transduction of the cells. A combination of such approaches can also be used. The VLPs can be produced either in vitro or in vivo.

VLPs can be produced in purified form by methods that are well-known to the skilled artisan, including centrifugation, as on sucrose or other layering substance, and by chromatography.

As used herein, "mutant" means that which is not wild-type. As used herein, "linked" refers but is not limited to fusion proteins formed by recombinant methods and chemical cross links. Suitable chemical cross links are well known to those skilled in the art.

In one embodiment, the protein is purified by one of the methods known to one skilled in the art.

This invention provides a vaccine which comprises a therapeutically effective amount of the above protein or complex. This invention also provides a vaccine which comprises a prophylactically effective amount of the above protein or complex.

This invention provides a method of stimulating or enhancing in a subject production of antibodies which recognize the above protein or complex.

This invention provides a method of stimulating or enhancing in a subject the production of cytotoxic T lymphocytes which recognize the above protein.

This invention provides an antibody capable of specifically binding to the above mutant protein. This invention also provides an antibody which is capable of specifically binding to the above mutant protein or complex but not to the wild type protein or complex.

This invention provides an antibody, antibody chain or fragment thereof identified using the viral envelope protein encoded by the above recombinant nucleic acid molecule. The antibody may be of the IgM, IgA, IgE or IgG class or subclasses thereof. The above antibody fragment includes but is not limited to Fab, Fab', (Fab')2, Fv and single chain antibodies. This invention provides a labeled antibody.

This invention provides an isolated antibody light chain of the above antibody, or fragment or oligomer thereof. This invention also provides an isolated antibody heavy chain of the above antibody, or fragment or oligomer thereof. This invention also provides one or more CDR regions of the above antibody. In one embodiment, the antibody is derivatized. In another embodiment, the antibody is a human antibody. The antibody includes but is not limited to monoclonal antibodies and polyclonal antibodies. In one embodiment, antibody is humanized.

As used herein "oligomer" means a complex of 2 or more subunits.

As used herein, "CDR" or complementarity determining region means a highly variable sequence of amino acids in the variable domain of an antibody.

As used herein, a "derivatized" antibody is one that has been modified. Methods of derivatization include but are not limited to the addition of a fluorescent moiety, a radionuclide, a toxin, an enzyme or an affinity ligand such as biotin.

As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA, IgE and IgM molecules. A "humanized" antibody would retain a similar antigenic specificity as the original antibody.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 and 5,693,761 and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 Å of the CDRs in a three dimensional model of the antibody and is predicted to be capable of interacting with the CDRs. The above methods are merely illustrative of some of the methods that one skilled in the art could employ to make humanized antibodies.

In one embodiment of the above antibodies, the viral envelope protein is derived from HIV-1.

As used herein "derived" means obtained in whole or in part from HIV in the form of genomic sequences, primary isolates, molecular clones, consensus sequences and encompasses chimeras, and sequences modified by means such as truncations and point mutations.

This invention provides an isolated nucleic acid molecule encoding the above antibody. The nucleic acid molecule includes but is not limited to RNA, genomic DNA and cDNA.

This invention provides a method of reducing the likelihood of a virally exposed subject from becoming infected with the virus comprising administering the above antibody or the above isolated nucleic acid, thereby reducing the likelihood of the subject from becoming infected with the virus. In a preferred embodiment, the virus is HIV.

As used herein, "reducing the likelihood" means a smaller chance than would exist in a control situation without administration of the nucleic acid, protein or antibody.

This invention provides a method of treating a subject infected with a virus comprising administering the above antibody or the above isolated nucleic acid, thereby treating the subject. In a preferred embodiment, the virus is HIV.

This invention provides an agent capable of binding the mutant viral envelope protein encoded by the above recombinant nucleic acid molecule. In one embodiment, the agent inhibits viral infection. In one embodiment, the viral envelope protein is derived from HIV-1.

As used herein, "agent" includes but is not limited to small organic molecules, antibodies, polypeptides, and polynucleotides.

As used herein, "inhibits viral infection" means reduces the amount of viral genetic information introduced into a target cell population as compared to the amount that would be introduced without said composition.

This invention provides a method for determining whether a compound is capable of inhibiting a viral infection comprising:

a. contacting an appropriate concentration of the compound with the mutant viral envelope protein encoded by the recombinant nucleic acid of claim 1 under conditions permitting binding of the compound to said protein;

B. contacting the resulting complex with a reporter molecule under conditions that permit binding of the reporter molecule to the mutant viral envelope protein; c. measuring the amount of bound reporter molecule; and d. comparing the amount of bound reporter molecule in step (C) with the amount determined in the absence of the compound, a decrease in the amount indicating that the compound is capable of inhibiting infection by the virus, thereby determining whether a compound is capable of inhibiting a viral infection.

Methods such as surface plasmon resonance may also be used to measure the direct binding of the compound to the mutant viral envelope protein using commercially available instruments, methods and reagents (Biacore, Piscataway, N.J.).

As used herein "reporter molecule" means a molecule which when bound to mutant envelope proteins can be detected. Such molecules include but are not limited to radio-labeled or fluorescently-labeled molecules, enzyme-linked molecules, biotinylated molecules or similarly affinity tagged molecules, or molecules which are reactive with antibodies or other agents that are so labeled.

As used herein "measuring" can be done by any of the methods known to those skilled in the art. These include but are not limited to fluorometric, calorimetric, radiometric or surface plasmon resonance methods.

In one embodiment, the reporter molecule is an antibody or derivative thereof. In one embodiment, the virus is HIV-1. In one embodiment, the reporter molecule comprises one or more host cell viral receptors or molecular mimics thereof.

As used herein "molecular mimics" means a molecule with similar binding specificity.

This invention provides a method for determining whether a compound is capable of inhibiting a viral infection which comprises:

a. contacting an appropriate concentration of the compound with a host cell viral receptor or molecular mimic thereof under conditions that permit binding of the compound and receptor or receptor mimic;

b. contacting the resulting complex with the mutant viral envelope protein encoded by the recombinant nucleic acid of claim 1 under conditions that permit binding of the envelope protein and receptor or receptor mimic in the absence of the compound;

c. measuring the amount of binding of envelope protein to receptor or receptor mimic;

d. comparing the amount of binding determined in step (c) with the amount determined in the absence of the compound, a decrease in the amount indicating that the compound is capable of inhibiting infection by the virus, thereby determining whether a compound is capable of inhibiting a viral infection.

In one embodiment of the above method, the virus is HIV-1. In one embodiment, the host cell viral receptor is CD4, CCR5, CXCR4 or combinations or molecular mimics thereof.

As used herein "CD4" means the mature, native, membrane-bound CD4 protein comprising a cytoplasmic domain, a hydrophobic transmembrane domain, and an extracellular domain which binds to the HIV-1 gp120 envelope glycoprotein. CD4 also comprises portions of the CD4 extracellular domain capable of binding to the HIV-1 gp120 envelope glycoprotein.

As used herein, "CCR5" is a chemokine receptor which binds members of the C—C group of chemokines and whose amino acid sequence comprises that provided in Genbank Accession Number 1705896 and related polymorphic variants. As used herein, CCR5 includes extracellular portions of CCR5 capable of binding the HIV-1 envelope protein.

As used herein, "CXCR4" is a chemokine receptor which binds members of the C—X—C group of chemokines and whose amino acid sequence comprises that provided in Genbank Accession Number 400654 and related polymorphic variants.

As used herein, CXCR4 includes extracellular portions of CXCR4 capable of binding the HIV-1 envelope protein.

This invention provides a compound isolated using the above methods.

Pharmaceutically acceptable carriers are well known to those skilled in the art and include but are not limited to 0.01–0.1M and preferably 0.05M phosphate buffer, phosphate-buffered saline, or 0.9% saline. Additionally, such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a compound determined to be capable of inhibiting a viral infection by the above methods.

This invention provides a pharmaceutical composition comprising an amount of the compound effective to inhibit viral infection determined by the above methods to be capable of inhibiting viral infection and a pharmaceutically acceptable carrier. In one embodiment, the viral infection is HIV infection. In the preferred embodiment, the viral infection is HIV-1 infection.

This invention provides a mutant complex comprising an immunodeficiency virus surface protein and an immunodeficiency virus transmembrane protein, wherein the mutant complex contains one or more mutations in amino acid sequence that enhance the stability of the complex formed between the viral surface protein and transmembrane protein, compared to the stability of the wildtype complex. In one embodiment, the stability of the complex is enhanced by introducing at least one disulfide bond between the transmembrane protein and the surface protein. In one embodiment, an amino acid residue in the transmembrane protein is mutated to a cysteine residue, resulting in the formation of a disulfide bond between the transmembrane protein and surface protein. In one embodiment, an amino acid residue in the surface protein protein is mutated to a cysteine residue, resulting in the formation of a disulfide bond between the transmembrane protein and surface protein. In one embodiment an amino acid residue in the transmembrane protein is mutated to a cysteine residue, and an amino acid residue in the surface protein protein is mutated to a cysteine residue, resulting resulting in the formation of a disulfide bond between the transmembrane protein and surface protein.

In one embodiment, immunodeficienecy virus is a human imunodeficiency virus. The human imunodeficiency virus includes but is not limited to the JR-FL strain. The surface protein includes but is not limited to gp120. An amino acid residue of the C1 region of gp120 may be mutated. An amino acid residue of the C5 region of gp120 may be mutated. The amino acids residues which may be mutated include but are not limited to the following amino acid residues: V35; Y39, W44; G462; I482; P484; G486; A488; P489; A492; and E500. The gp120 amino acid residues are also set forth in FIG. 3A. The transmembrane protein includes but is not limited to gp41. An amino acid in the ectodomain of gp41 may be mutated. The amino acids residues which may be mutated include but are not limited to the following amino acid residues: D580; W587; T596; V599; and P600. The gp41 amino acid residues are also set forth in FIG. 3B.

This invention provides a mutant viral envelope protein which differs from the corresponding wild type protein in at least one amino acid which yields a complex comprising a surface protein and a transmembrane protein which has enhanced stability relative to the corresponding complex obtained from the wild type envelope protein, wherein the surface protein and transmembrane protein are encoded by different nucleic acids.

This invention provides a complex comprising a viral surface protein and a viral transmembrane protein which has enhanced stability relative to the corresponding complex obtained from the wildtype envelope protein, yielded by the proteolysis of a mutant viral envelope protein with a sequence which differs from the corresponding wild type protein sequence in at least one amino acid, wherein the surface protein and transmembrane protein are encoded by different nucleic acids.

This invention provides a nucleic acid which encodes a mutant surface protein wherein the surface protein is complexed with its corresponding transmembrane protein and will have enhanced stability.

This invention provides a nucleic acid which encodes a mutant transmembrane protein wherein the transmembrane protein is complexed with its corresponding surface protein and will have enhanced stability.

This invention provides an antibody which binds to the above protein or above complex but does not cross react with the individual monomeric surface protein or the individual monomeric transmembrane protein.

This invention provides the above antibody capable of binding to the virus.

This invention provides a protein comprising at least a portion of a viral envelope protein which differs from the corresponding wild type protein in at least one amino acid which yields a complex comprising a surface protein and a transmembrane protein which has enhanced stability relative to the corresponding complex obtained from the wild type envelope protein, wherein the portion of the protein results in enhanced stability.

This invention provides a portion of the above protein, wherein the portion results in enhanced immunogenicity in comparison to the corresponding wild type portion.

This invention further provides a simple method for determining whether a subject has produced antibodies capable of blocking the infectivity of a virus. This diagnostic test comprises examining the ability of the antibodies to bind to the stabilized viral envelope protein. As shown herein, such binding is indicative of the antibodies' ability to neutralize the virus. In contrast, binding of antibodies to non-stabilized, monomeric forms of viral envelope proteins is not predictive of the antibodies' ability to bind and block the infectivity of infectious virus (Fouts et al., J. Virol. 71:2779, 1997). The method offers the practical advantage of circumventing the need to use infectious virus.

Numerous immunoassay formats that are known to the skilled artisan are appropriate for this diagnostic application. For example, an enzyme-linked immunosorbent assay (ELISA) format could be used wherein in the mutant virus envelope glycoprotein is directly or biospecifically captured onto the well of a microtiter plate. After wash and/or blocking steps as needed, test samples are added to the plate in a range of concentrations. The antibodies can be added in a variety of forms, including but not limited to serum, plasma, and a purified immunoglobulin fraction. Following suitable incubation and wash steps, bound antibodies can be detected, such as by the addition of an enzyme-linked reporter antibody that is specific for the subject's antibodies. Suitable enzymes include horse radish peroxidase and alkaline phosphatase, for which numerous immunoconjugates and calorimetric substrates are commercially available. The binding of the test antibodies can be compared with that of a known monoclonal or polyclonal antibody standard assayed in parallel. In this example, high level antibody binding would indicate high neutralizing activity.

As an example, the diagnostic test could be used to determine if a vaccine elicited a protective antibody response in a subject, the presence of a protective response indicating that the subject was successfully immunized and the lack of such response suggesting that further immunizations are necessary. In a preferred embodiment, the subject is a human.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

1. Materials

The plasmid designated PPI4-tPA-gp120$_{JR-FL}$ was deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 75431. The plasmid was deposited with ATCC on Mar. 12, 1993. This eukaryotic shuttle vector contains the cytomegalovirus major immediate-early (CMV MIE) promoter/enhancer linked to the full-length HIV-1 envelope gene whose signal sequence was replaced with that derived from tissue plasminogen activator. In the vector, a stop codon has been placed at the gp120 C-terminus to prevent translation of gp41 sequences, which are present in the vector. The vector also contains an ampicillin resistance gene, an SV40 origin of replication and a DHFR gene whose transcription is driven by the β-globin promoter.

The epitopes for, and some immunochemical properties of, anti-gp120 Mabs from various donors have been described previously (Moore et al., J. Virol. 768: 469, 1994; Moore and Sodroski, J. Virol. 70:1863, 1996). These include Mab 19b to the V3 locus (Moore et al., J. Virol. 69:122, 1995); mABs 50.1 and 83.1 to the V3 loop (White-Scharf et al. Virology 192:197, 1993); MAbs IgG1b12 and F91 to the CD4 binding site (CD4bs) (Burton et al., Science 266: 124, 1994; Moore and Sodroski, J. Virol. 70:1863, 1996) Mab 2G12 to a unique C3-V4 glycan-dependent epitope (Trkola et al., J. Virol. 70:1100, 1996) MAb M90 to the C1 region (diMarzo Veronese et al. AIDS Res. Human Retrov. 8:1125, 1992); Mab 23a and Ab D7324 to the CS region (Moore and Sodroski, J. Virol. 70:1863, 1996); Mab 212A to a conformational C1–C5 epitope (Moore et al. J. Virol 68:6836, 1994); Mab 17b to a CD4-inducible epitope (Moore and Sodroski, J. Virol. 70:1863, 1996); Mab A32 to a CD4-inducible C1–C4 epitope (Moore and Sodroski, J. Virol. 70:1863, 1996; Sullivan et al, J. Virol. 72:4694, 1998); Mabs G3-519 and G3-299 to C4 or C4/V3 epitopes (Moore and Sodroski, J. Virol. 70:1863, 1996). Mabs to gp41 epitopes included 7B2 to epitope cluster 1 (kindly provided by Jim Robinson, Tulane University); 25C2 to the fusion peptide region (Buchacher et al. AIDS Res. Human Retrov. 10:359, 1994); 2F5 to a neutralizing epitope encompassing residues 665–690 (Munster et al. J. Virol. 68:4031, 1994). The tetrameric CD4-IgG2 has been described previously (Allaway et al. AIDS Res. Human Retrovir. 11:533, 1995).

Anti-HIV Abs were obtained from commercial sources, from the NIH AIDS Reagent Program, or from the inventor. Where indicated, the Abs were biotinylated with NHS-biotin (Pierce, Rockford, Ill.) according to the manufacturer's instructions.

Monomeric gp120$_{JR-FL}$ was produced in CHO cells stably transfected with the PPI4-tPA-gp120$_{JR-FL}$ plasmid as described (U.S. Pat. Nos. 5,866,163 and 5,869,624). Soluble CD4 was purchased from Bartels Corporation (Issaquah, Wash.).

2. Construction of PPI4-based Plasmids Expressing Wild-type and Mutant HIV Envelope Proteins Wild-type gp140s (gp140WT) The gp140 coding sequences were amplified using the polymerase chain reaction (PCR) from full-length molecular clones of the HIV-1 isolates JR-FL, DH123, Gun-1, 89.6, NL4-3 and HxB2. The 5' primer used was designated Kpn1env (5'-GTCTATTATGGGGTACCTGTGTGGAA AGAAGC-3') (SEQ ID NO:3) while the 3' primer was BstB1env (5'-CGCAGACGCAGATTCGAATTAATACCACAGCCA GTT-3') (SEQ ID NO:4). PCR was performed under stringent conditions to limit the extent of Taq polymerase-introduced error. The PCR products were digested with the restriction enzymes Kpn1 and Xho1 and purified by agarose gel electrophoresis. Plasmid PPI4-tPA-gp120$_{JR-FL}$ was also digested with the two restriction enzymes and the large fragment (vector) was similarly gel-purified. The PPI4-tPA-gp120$_{JR-FL}$ expression vector has been described previously (Hasel and Maddon, U.S. Pat. Nos. 5,886,163 and 5,869,624). Ligations of insert and vector were carried out overnight at room temperature. DH5αF'Q10 bacteria were transformed with 1/20 of each ligation. Colonies were screened directly by PCR to determine if they were transformed with vector containing the insert. DNA from three positive clones of each construct were purified using a plasmid preparation kit (Qiagen, Valencia, Calif.) and both strands of the entire gp160 were sequenced. By way of example, pPPI4-gp140WT$_{JR-FL}$ and pPPI4-gp140WT$_{DH123}$ refer to vectors expressing wild-type, cleavable gp140s derived from HIV-1$_{JR-FL}$ and HIV-1$_{DH}$123, respectively.

gp140UNC A gp120-gp41 cleavage site mutant of JR-FL gp140 was generated by substitutions within the REKR motif at the gp120 C-terminus, as described previously. (Earl et al., Proc. Natl. Acad. Sci. USA 87:648, 1990). The deletions were made by site-directed mutagenesis using the mutagenic primers 5'140M (5'-CTACGACTTCGTCTCCGCCTT CGACTACGGGGAAT-AGGAGCTGTGTTCCTTGGGT TCTTG-3')(SEQ ID NO:5) and 3'gp140M (sequence conjunction with Kpn1env and BstB1env 5'-TCGAAGGCGGAGACGAAGTCGTAGCCGCAGTG CCTTGGTGG GTGCTACTCCTAATGGTTC-3')(SEQ ID NO:6). In conjunction with Kpn1env and BstB1, the PCR product was digested with Kpn1 and BstB1 and subcloned into pPPI4 as described above.

Loop-deleted gp120s and gp140s PPI4-based plasmids expressing variable loop-deleted forms of gp120 and gp140 proteins were prepared using the splicing by overlap extension method as described previously (Binley et al., AIDS Res. Human Retrovir. 14:191, 1998). In the singly loop-deleted mutants, a Gly-Ala-Gly spacer is used to replace D132-K152 (ΔV1), F156-I191 (ΔV2), or T300-G320 (ΔV3). The numbering system corresponds to that for the JR-FL clone of HIV-1 (Genbank Accession #U63632).

PCR amplification using DGKPN5'PPI4 and 5JV1V2-B (5'-GTCTATTATGGGGTACCTGTGTGGAAAGAAGC-3')(SEQ ID NO:7) on a ΔV1 template and subsequent digestion by Kpn1 and BamH1 generated a 292 bp fragment lacking the sequences encoding the V1 loop. This fragment was cloned into a plasmid lacking the sequences for the V2 loop using the Kpn1 and BamH1 restriction sites. The resulting plasmid was designated ΔV1V2' and contained a Gly-Ala-Gly sequences in place of both D132-K152 and F156-I191. Envs lacking the V1, V2 and V3 loops were generated in a similar way using a fragment generated by PCR on a ΔV3 template with primers 3JV2-B (5'-GTCTGAGTCGGATCCTGTGACACCTCAGTCATTA CACAG-3')(SEQ ID NO:8) and H6NEW (5' CTC-GAGTCTTCGAATTAGTGATGGGT GATGGTGATGATACCACAGCCATTTGTTATGTC-3') (SEQ ID NO:9). The fragment was cloned into ΔV1V2', using BamH1 and BstB1. The resulting env construct was named ΔV1V2'V3. The glycoproteins encoded by the ΔV1V2' and ΔV1V2'V3 plasmids encode a short sequence of amino acids spanning C125 to C130. These sequences were removed using mutagenic primers that replace T127-I191 with a Gly-Ala-Gly sequence. We performed PCR amplification with primers 3'DV1V2STU1 (5'-GGCTCAAAGGATATCTTTGGACAGGCCTGT GTAAT-GACTGAGGTGTCACATCCTGCACCACAGA GTGGGGTTAATTTTACACATGGC-3') (SEQ ID NO:10) and DGKPN5' PPI4, digested the resulting fragment by Stu1 and Kpn1 and cloned it in a PPI4 gp140 vector. The resulting gp140 was named ΔV1V2*. In an analogous manner ΔV1V2*V3 was constructed. The amino acid substitutions are shown schematically in FIG. 10.

Disulfide-stabilized gp140s The indicated amino acids in gp120 and gp41 were mutated in pairs to cysteines by site-directed mutagenesis using the Quickchange kit (Stratagene, La Jolla, Calif.). As indicated below, additional amino acids in the vicinity of the introduced cysteines were mutated to alanines using similar methods in an attempt to better accommodate the cysteine mutations within the local topology of the envelope glycoproteins. The changes were similarly made on templates encoding both wild-type and loop-deleted HIV envelope proteins.

3. Expression of gp140s in Transiently Transfected 293T Cells

HIV envelope proteins were transiently expressed in adherent 293T cells, a human embryonic kidney cell line (ATCC Cat. #CRL-1573) transfected with the SV40 large T antigen, which promotes high level replication of plasmids such as PPI4 that contain the SV40 origin. 293T cells were grown in Dulbecco's minimum essential medium (DMEM; Life Technologies, Gaithersburg, Md.) containing 10% fetal bovine serum supplemented with L-glutamine, penicillin, and streptomycin. Cells were plated in a 10 cm dish and transfected with 10 μg of purified PPI4 plasmid using the calcium phosphate precipitation method. On the following day, cells were supplied fresh DMEM containing 0.2% bovine serum albumin along with L-glutamine, penicillin and streptomycin. For radioimmunoprecipitation assays, the medium also contained $^{35}$S-labeled cysteine and methionine (200 μCi/plate). In certain experiments, the cells were cotransfected with 10 μg of a pcDNA3.1 expression vector (Invitrogen, Carlsbad, Calif.) encoding the gene for human furin.

4. ELISA Analyses

The concentration of gp120 and gp140 proteins in 293T cell supernatants was measured by ELISA (Binley et al. J. Virol 71:2799, 1997). Briefly, Immulon II ELISA plates (Dynatech Laboratories, Inc.) were coated for 16–20 hr at 4° C. with a polyclonal sheep antibody that recognizes the carboxy-terminal sequence of gp120 (APTKAKRRVVQREKR) (SEQ ID NO:11). The plate was washed with tris buffered saline (TBS) and then blocked with 2% nonfat milk in TBS. Cell supernatants (100 μL) were added in a range of dilutions in tris buffered saline containing 10% fetal bovine serum. The plate was incubated for 1 hr at ambient temperature and washed with TBS. Anti-gp120 or anti-gp41 antibody was then added for an additional hour. The plate was washed with TBS, and the amount of bound antibody is detected using alkaline phosphatase conjugated goat anti-human IgG or goat anti-mouse IgG. Alternatively, biotinylated reporter Abs are used according to the same procedure and detected using a streptavidin-AP conjugate. In either case, AP activity is measured using the AMPAK kit (DAKO) according to the manufacturer's instructions. To examine the reactivity of denatured HIV envelope proteins, the cell supernatants were boiled for 5 minutes in the presence of 1% of the detergents sodium dodecyl sulfate and NP-40 prior to loading onto ELISA plates in a range of dilutions. Purified recombinant JR-FL gp120 was used as a reference standard.

5. Radioimmunoprecipitation Assay (RIPA)

$^{35}$S-labeled 293T cell supernatants were collected 2 days post-transfection for RIPA analysis. Culture supernatants were cleared of debris by low speed centrifugation (~300g) before addition of RIPA buffer to a final concentration of 50 mM tris-HCl, 150 mM NaCl, 5 mM EDTA, pH 7.2. Biotinylated Abs (~10 μg) were added to 1 mL of supernatant and incubated at ambient temperature for 10 min. Samples were then incubated with streptavidin-agarose beads for 12–18hr at 4° C. with gentle agitation. Alternatively, unlabeled Abs were used in combination with protein G-agarose (Pierce, Rockford, Ill.). The beads were washed three times with RIPA buffer containing 1% Nonidet-P40 (NP40) detergent. Bound proteins were eluted by heating at 100° C. for 5 min with SDS-PAGE sample buffer containing 0.05 M tris-HCl, 10% glycerol, 2% sodium dodecyl sulfate (SDS), 0.001% bromophenol blue, and where indicated, 100 mM dithiothreitol (DTT). Samples were loaded on an 8% polyacrylamide gel and run at 200V for 1 hour. Gels were then dried and exposed to a phosphor screen for subsequent image analysis using a STORM phosphoimager (Molecular Dynamics, Sunnyvale, Calif.). $^{14}$C-labeled proteins were used as size calibration standards (Life Technologies, Gaithersburg, Md.).

Experimental Results

1. Processing of gp140NON is Facilitated by Co-expression of the Furin Protease

Figure 2:
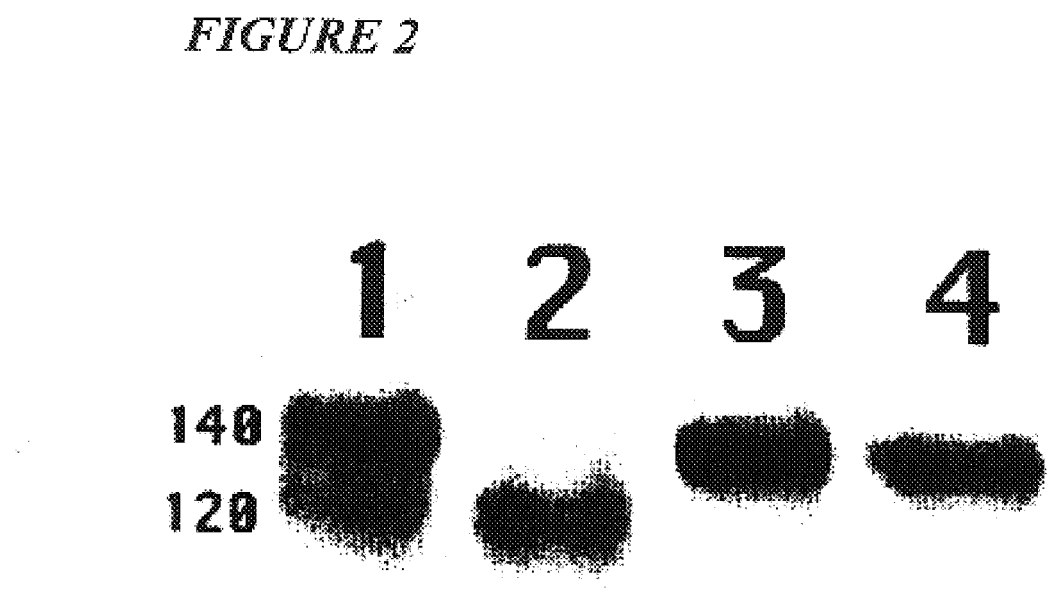

To minimize the production of gp140NON, pcDNA3.1-furin and pPPI4-gp140WT$_{JR-FL}$ were cotransfected into 293T cells, and RIPA assay was performed using the anti-gp120 MAb 2G12. As indicated in FIG. 2, furin eliminated production of gp140NON but had no effect on gp140UNC. Similar results were obtained in RIPAs performed using other anti-gp120 MAbs (data not shown).

Treatment of the samples with DTT prior to SDS-PAGE did not affect the migration or relative amounts of these bands, indicating that the gp140s consist of a single polypeptide chain rather than separate gp120-gp41 molecules linked by an adventitious disulfide bond.

2. Stabilization of the gp120-gp41 Interaction by Introduction of Double Cysteine Mutations With furin co-transfection, we could now express a soluble gp140 protein in which the gp120 and gp41ECTO components were associated only through a non-covalent linkage, mimicking what occurs in the native trimeric envelope glycoprotein complex on virions. However, on virions or the surface of infected cells, the gp120-gp41 association is weak, so that gp120 is gradually shed (McKeating et al. J. Virol 65:852, 1991). We found this to occur also with the gp140WT protein made in the presence of endogenous furin. Thus, we could detect very little, if any, stable gp120-gp41ECTO complexes in the supernatants from gp140WT-expressing cells after immunoprecipitation. We therefore sought ways to stabilize the non-covalent gp120-gp41 interaction, by the introduction of an intermolecular disulfide bond between the gp120 and gp41 subunits.

Figure 3A:
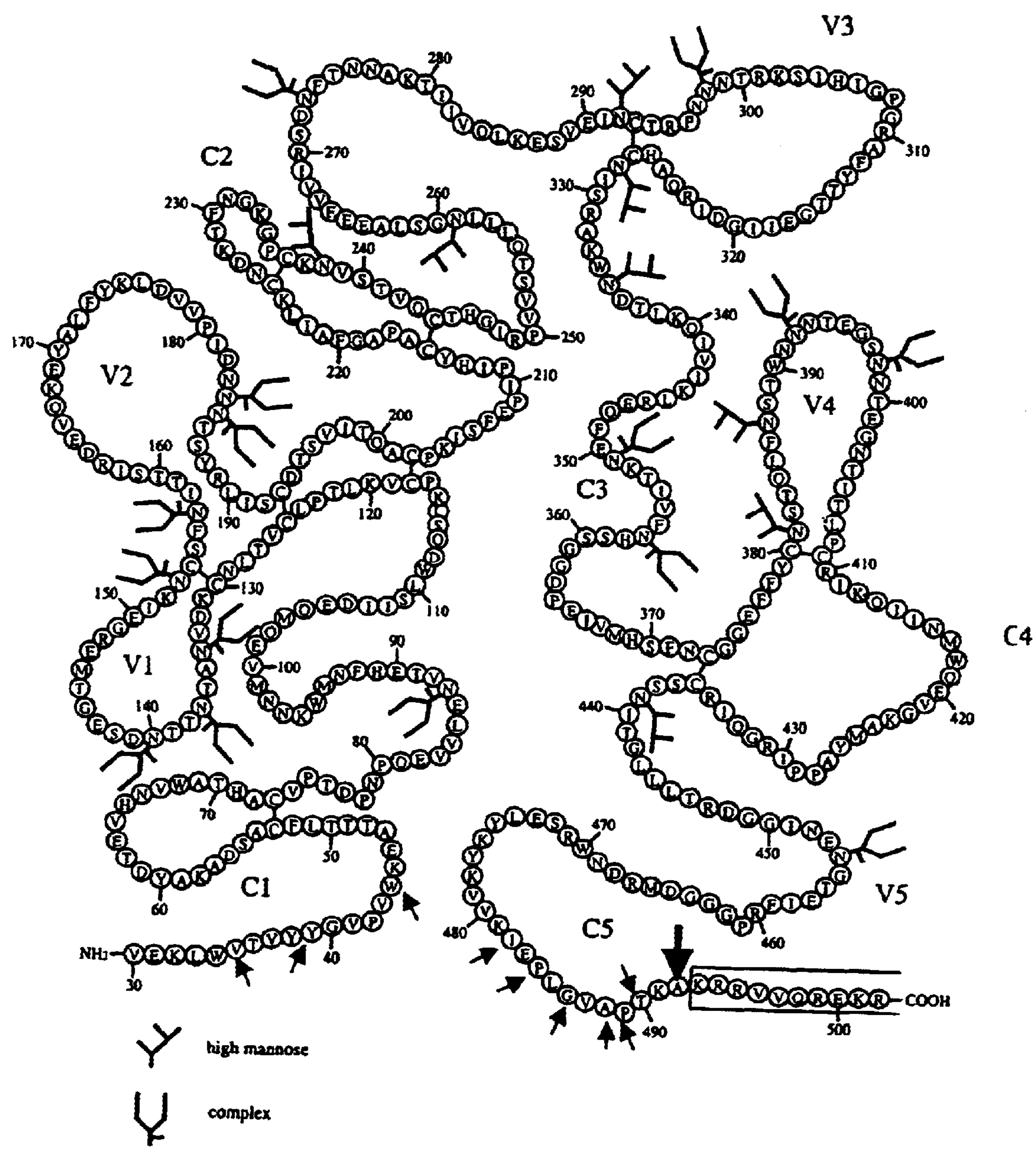
Figure 3B:
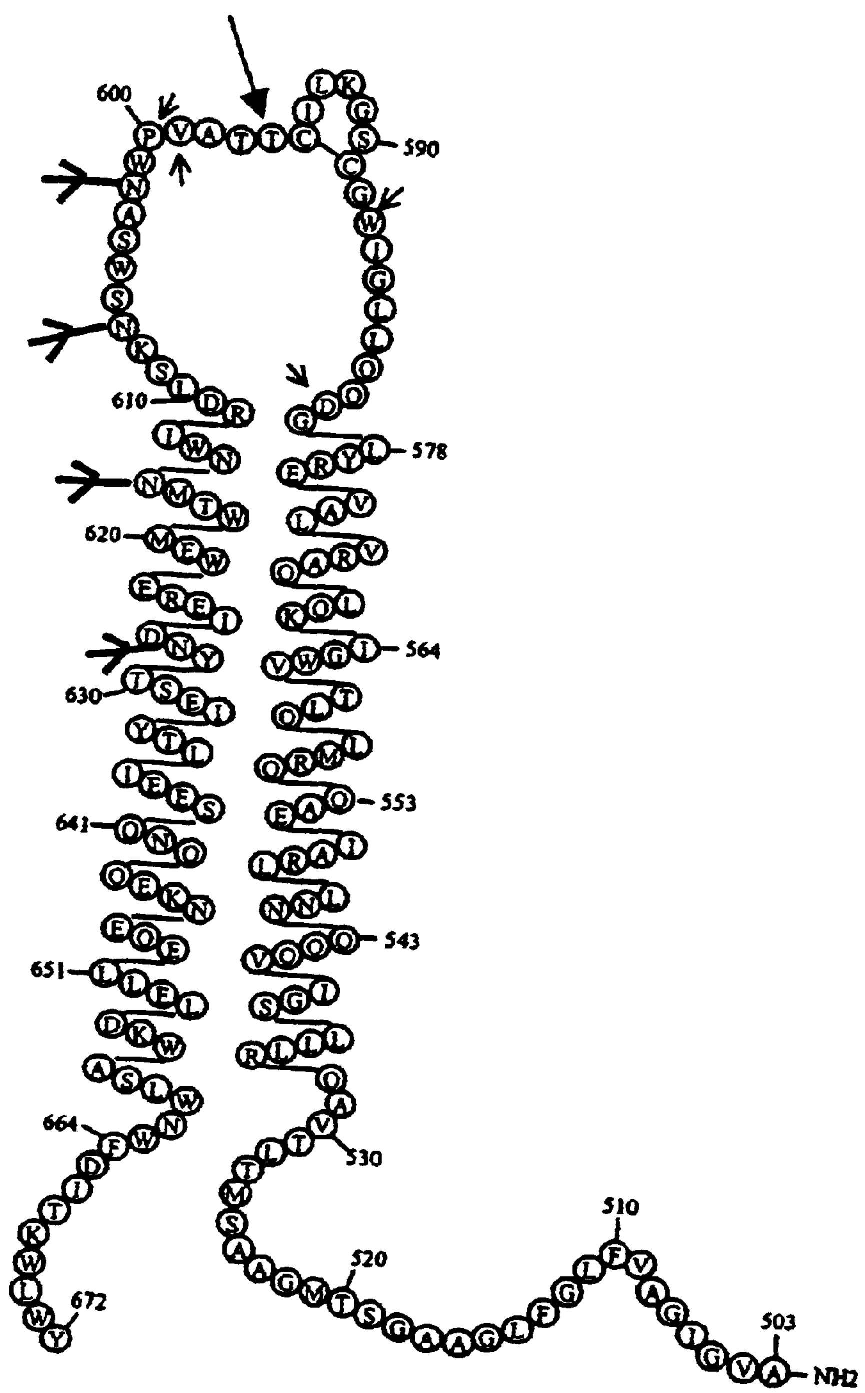
Figure 4:
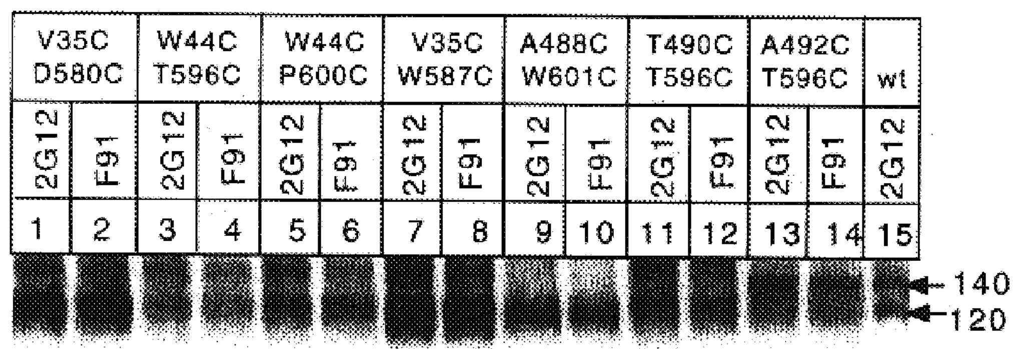

We therefore substituted a cysteine residue at one of several different positions in the C1 and C5 regions of gp120, focussing on amino acids previously shown to be important for the gp120-gp41 interaction (FIG. 3*a*). Simultaneously, we introduced a second cysteine mutation at several residues near the intramolecular disulfide loop of gp41 (FIG. 3*b*). The intent was to identify pairs of cysteine residues whose physical juxtaposition in native gp120-gp41 was such that an intermolecular disulfide bond would form spontaneously. In all, >50 different double-cysteine substitution mutants were generated in the context of the JR-FL gp140WT protein, and co-expressed with furin in transient transfections of 293T cells An initial analysis of the transfection supernatants by antigen capture ELISA indicated that all of the mutants were efficiently expressed as secreted proteins, except those which contained a cysteine at residue 486 of gp120 (data not shown). We next characterized the transfection supernatants by immunoprecipitation with the anti-gp120 MAbs 2G12 and F91 (FIG. 4). In addition to the expected 120 kDa band (gp120), a second band of approximately 140 kDa was precipitated by F91 and 2G12 from many of the double-cysteine mutant transfection supernatants. The gp140 bands derived from mutants in which a cysteine was present in the C1 region of gp120 migrated slightly more slowly, and were more diffuse, than the corresponding bands from mutants in which the gp120 cysteine was in the C5 region (FIG. 4). The presence of diffuse bands with reduced mobility on SDS-PAGE gels is probably indicative of incomplete or improper envelope glycoprotein processing, based on previous reports (Earl et al. Proc. Natl. Acad. Sci. USA 87:648, 1990; Earl et al. J. Virol 68:3015, 1994). The relative intensity of the 140 kDa band was highly dependent upon the positions of the introduced cysteines, suggesting that certain steric requirements must be met if a stable intersubunit disulfide bond is to be formed.

To determine which among the double-cysteine mutants was the most suitable for further analysis, we determined the relative intensities of the gp140 and gp120 bands derived after immunoprecipitation of each mutant by the potently neutralizing anti-gp120 MAb 2G12, followed by SDS-PAGE and densitometry (FIG. 5). We sought the mutant for which the gp140/gp120 ratio was the highest, which we interpreted as indicative of the most efficient formation of the intermolecular disulfide bond. From FIG. 5, it is clear that mutant A492C/T596C has this property. From hereon, we will refer to this protein as the SOS gp140 mutant. Of note is that the mobility of the SOS gp140 mutant on SDS-PAGE is identical to that of the gp140NON protein, in which the gp120 and gp41ECTO moieties are linked by a peptide bond. The gp140 band derived from the SOS mutant is not quite as sharp as that from the gp140NON protein, but it is less diffuse than the gp140 bands obtained from any of the other double-cysteine mutants (FIG. 4). This suggests that the SOS mutant is efficiently processed. The complete nucleic acid and amino acid sequences of the JR-FL SOS gp140 mutant are provided in FIG. 13.

Figure 6A:
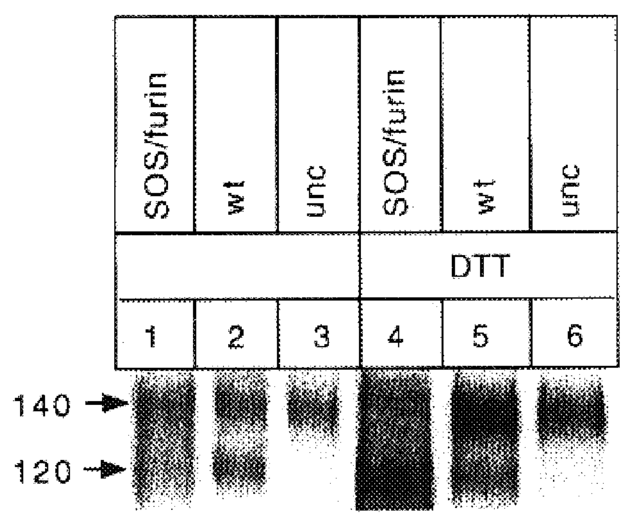
Figure 6B:
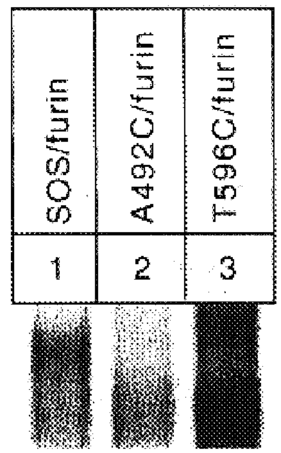
Figure 6C:
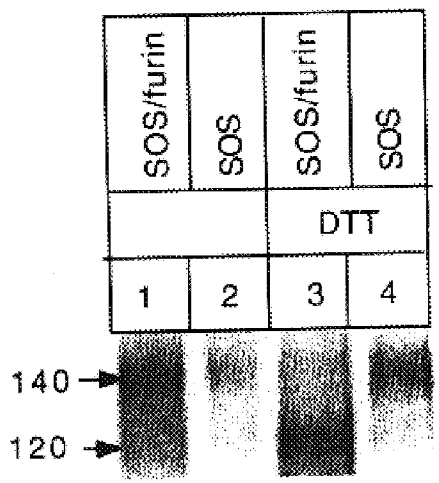

We verified that the 140 kDa proteins were stabilized by an intermolecular disulfide bond by treating the immunoprecipitated proteins with DTT prior to gel electrophoresis. In contrast, the 140 kDa bands in gp140WT and gp140UNC were unaffected by the DTT treatment as expected for uncleaved single-chain proteins. Of note is that a 140 kDa band was never observed for either the A492C or T596C single mutants.(FIG. 6*b*). This is further evidence that the 140 kDa band in the double-cysteine mutants arises from the formation of an intermolecular disulfide bond between gp120 and gp41ECTO. In the absence of exogenous furin, the 140 kDa SOS protein band was not reducible by DTT, suggesting the band is the double cysteine mutant of gp140NON (FIG. 6C).

3. Approaches to Improve the Efficiency of Disulfide Bond Formation in the SOS gp140 Protein Disulfide-stabilized gp140 is not the only env species present in the 293T cell supernatants. Discernable amounts of free gp120 are also present. This implies that the disulfide bond between gp120 and the gp41 ectodomain forms with imperfect efficiency. Although the free gp120 can be removed by the purification methods described below, attempts were made to further reduce or eliminate its production. To this end, additional amino acid substitutions were made near the inserted cysteines. In addition, the position of the cysteine in gp120 was varied. We retained the gp41 cysteine at residue 596, as in the SOS gp140 protein, because this position seemed to be the one at which intermolecular disulfide bond formation was most favored.

Figure 7:
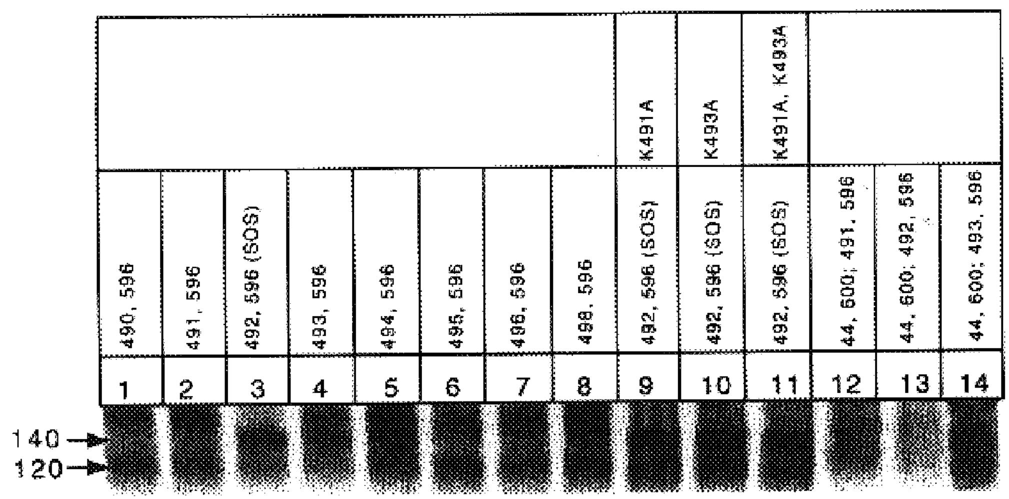

We first varied the position of the cysteine substitution in gp120, by placing it either N-terminal or C-terminal to alanine-492. The gp140/gp140+gp120 ratio was not increased in any of these new mutants; it remained comparable with, or less than, the ratio derived from the SOS gp140 protein (FIG. 7). Furthermore, there was usually a decrease in the mobility and sharpness of the gp140 band compared to that derived from the SOS gp140 protein (FIG. 7). Next, we considered whether the bulky side chains of the lysine residues adjacent to alanine-492 might interfere with disulfide bond formation. We therefore mutated the lysines at positions 491 and 493 to alanines in the context of the SOS gp140 protein, but these changes neither increased the gp140/gp140+gp120 ratio nor affected the migration of gp140 (FIG. 7). Finally, we introduced a second pair of cysteines into the SOS gp140 protein at residues 44 of gp120 and 600 of gp41, since a disulfide bond formed fairly efficiently when this cysteine pair was introduced into the wild-type protein (FIG. 5). However, the quadruple-cysteine mutant (W44C/A492C/P600C/T596C) was poorly expressed, implying that there was a processing or folding problem (FIG. 7). Poor expression was also observed with two more quadruple-cysteine mutants (W44C/K491C/P600C/T596C and (W44C/K493C/P600C/T596C) (FIG. 7).

Further approaches to optimize the efficiency or overall expression of the disulfide stabilized mutant are possible. For example, cells stably transfected with furin could be created so as to ensure adequate levels of furin in all cells expressing the SOS gp140 proteins. Similiarly, furin and the gp140 proteins could be coexpressed from a single plasmid. K491 and K493 could be mutated to non-alanine residues singly or as a pair. To better accomodate the introduced cysteines, other gp120 and/or gp41 amino acids in the vicinity of the introduced cysteines could be mutated as well.

4. The Antigenicity of the SOS gp140 Protein Parallels That of Virus-associated gp120-gp41

Compared to gp140NON, the SOS gp140 protein has several antigenic differences that we believe are desirable for a protein intended to mimic the structure of the virion-associated gp120-gp41 complex. These are summarized below.

1) The SOS gp140 protein binds strongly to the potently neutralizing MAbs IgG1b12 and 2G12, and also to the CD4-IgG2 molecule (FIG. 8*a*). Although the RIPA methodology is not sufficiently quantitative to allow a precise determination of relative affinities, the reactivities of these MAbs and of the CD4-IgG2 molecule with the SOS gp140 protein appear to be substantially greater than with the gp140NON and gp120 proteins (FIG. 8*a*). Clearly, the SOS gp140 protein has an intact CD4-binding site. V3 loop epitopes are also accessible on the SOS gp140 protein, shown by its reactivity with MAbs 19b and 83.1 (FIG. 8*a*).

2) Conversely, several non-neutralizing anti-gp120 MAbs bind poorly, or not at all, to the SOS gp140 protein whereas they react strongly with gp140NON and gp120 (FIG. 8*b*). These MAbs include ones directed to the C1 and C5 domains, regions of gp120 that are involved in gp41 association and which are considered to be occluded in the context of a properly formed gp120-gp41 complex (Moore et al. J. Virol 68:469, 1994; Wyatt et al. J. Virol. 71:9722, 1997). Conversely, the C1 and C5-directed MAbs all reacted strongly with the gp140NON protein (FIG. 8*b*).

3) The exposure of the epitope for MAb 17b by the prior binding of soluble CD4 occurs far more efficiently on the SOS gp140 protein than on the gp140NON or gp120 proteins (FIG. 8*c*). Indeed, in the absence of soluble CD4, there was very little reactivity of 17b with the SOS gp140 protein. The CD4-induced epitope for MAb 17b overlaps the coreceptor binding site on gp120; it is considered that this site becomes exposed on the virion-associated gp120-gp41 complex during the conformational changes which initiate virus-cell fusion after CD4 binding. Induction of the 17b epitope suggests that the gp120 moieties on the SOS gp140 protein possess the same static conformation and conformational freedom as virus-associated gp120-gp41. The gp140NON protein bound 17b constitutively, and although there was some induction of the 17b epitope upon soluble CD4 binding, this was less than occurred with the SOS gp140 protein.

4) Another CD4-inducible epitope on gp120 is that recognized by MAb A32 (Moore et al. J. Virol. 70:1863, 1996; Sullivan et al. J. Virol. 72:4694, 1998). There was negligible binding of A32 to the SOS gp140 mutant in the absence of soluble CD4, but the epitope was strongly induced by soluble CD4 binding (FIG. 8*c*). As observed with 17b, the A32 epitope was less efficiently induced on the gp140NON protein than on the SOS gp140 protein.

Figure 8D:
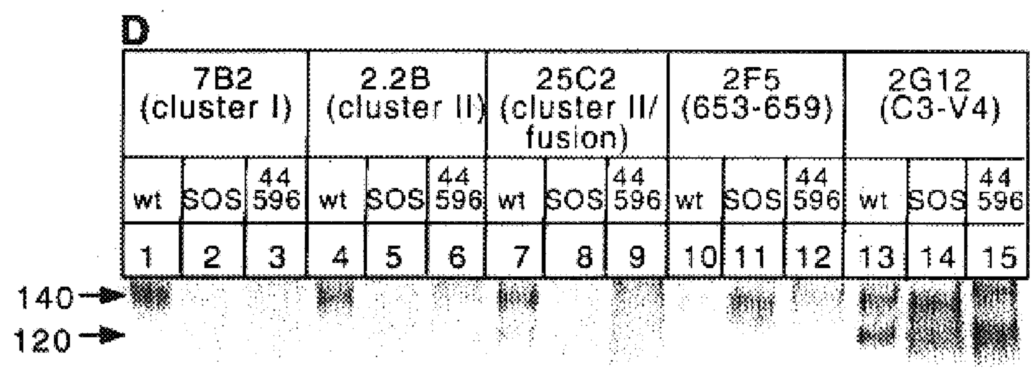

5) There was no reactivity of any of a set of non-neutralizing gp41 MAbs with the SOS gp140 protein, whereas all of these MAbs bound strongly to the gp140NON protein. These anti-gp41 MAbs recognize several regions of the gp41 ectodomain, all of which are thought to be occluded by gp120 in the virion-associated gp120-gp41 complex (Moore et al. J. Virol. 68:469, 1994; Sattentau et al. Virology 206:713, 1995). Their failure to bind to the SOS gp140 protein is another strong indication that this protein adopts a configuration similar to that of the native trimer; their strong recognition of the gp140NON protein is consistent with the view that these proteins have an aberrant conformation because of the peptide bond linking gp120 with gp41 (Edinger et al. J. Virol. 73:4062, 1999)(FIG. 8*d*).

6) In marked contrast to what was observed with the non-neutralizing MAbs, the neutralizing anti-gp41

MAb 2F5 bound efficiently to the SOS gp140 protein, but not to the gp140NON protein. Of note is that the 2F5 epitope is the only region of gp41 thought to be well exposed in the context of native gp120-gp41 complexes (Sattentau et al. Virology 206: 713, 1995). Its ability to bind 2F5 is again consistent with the adoption by the SOS gp140 protein of a configuration similar to that of the native trimer.

The antigenic properties of the SOS gp140 protein were compared with those of the W44C/T596C gp140 mutant. Among the set of mutants that contained a cysteine substitution within the C1 domain, this was the most efficient at gp140 formation. Although the W44C/T596C gp140 reacted well with the 2G12 MAb, it bound CD4-IgG2 and IgG1b12 relatively poorly. Furthermore, there was little induction of the 17b epitope on the W44C/T596C gp140 by soluble CD4, yet strong reactivity with non-neutralizing anti-gp41 MAbs (FIG. 8). We therefore judge that this mutant has suboptimal antigenic properties. Indeed, the contrast between the properties of the W44C/T596C gp140 protein and the SOS gp140 protein demonstrates that the positioning of the intermolecular disulfide bonds has a significant influence on the antigenic structure of the resulting gp140 molecule.

Figure 8E:
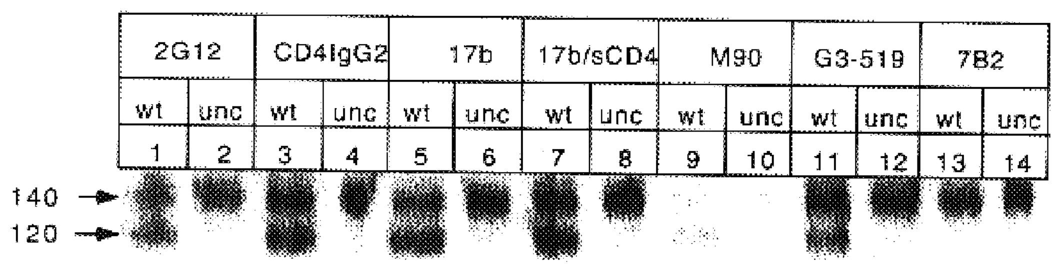

In contrast to the antigenic character of the gp140SOS protein, the 140 kDa proteins of gp140WT and gp140UNC reacted strongly with non-neutralizing anti-gp120 and anti-gp41 MAbs such as G3-519 and 7B2. In addition, the epitope recognized by MAb 17B was constitutively exposed rather than CD4-inducible (FIG. 8*e*).

Overall, there was a strong correlation between the binding of MAbs to the SOS gp140 protein and their ability to neutralize HIV-$1_{JR-FL}$. This correlation was not observed with the gp140NON, gp140UNC or gp120 proteins.

5. The Formation of Intersubunit Disulfide Bonds is not Isolate-dependent

Figure 9A:
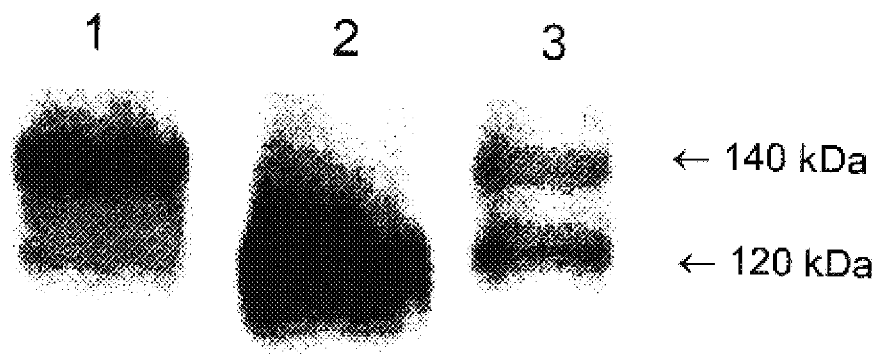
Figure 9B:
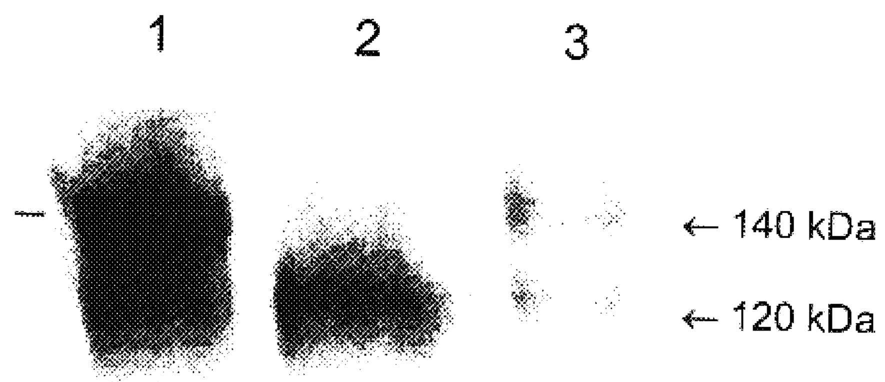

To assess the generality of our observations with gp140 proteins derived from the R5 HIV-1 isolate JR-FL, we generated double-cysteine mutants of gp140's from other HIV-1 strains. These include the R5X4 virus DH123 and the X4 virus HxB2. In each case, the cysteines were introduced at the residues equivalent to alanine-492 and threonine-596 of JR-FL. The resulting SOS proteins were transiently expressed in 293T cells and analyzed by RIPA to ascertain their assembly, processing and antigenticity. As indicated in FIG. 9, 140 kDa material is formed efficiently in the DH123 and HxB2 SOS proteins, demonstrating that our methods can successfully stabilize the envelope proteins of diverse viral isolates.

6. Disulfide Stabilization of HIV Envelope Proteins Modified in Variable Loop and Glycosylation Site Regions Since there is evidence to suggest that certain variable loop and glycosylation site mutations provide a means to better expose underlying conserved neutralization epitopes, we examined the assembly and antigenicity of disulfide-stabilized forms. In initial studies, A492C/T596C JR-FL gp140 mutants were created for each of the ΔV1, ΔV2, ΔV3, ΔV1V1*, and ΔV1V2*V3 molecules described above. For the ΔV1V2*V3 protein, glycosylation site mutants were also synthesized by N→Q point mutations of amino acids 357 and 398.

Figures 11A, 11B:
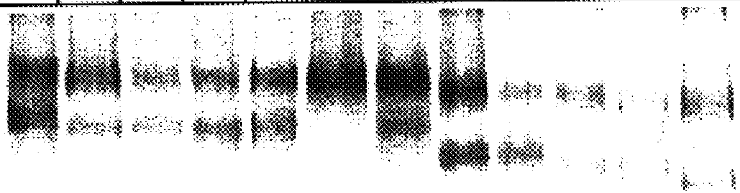
Figure 12A:
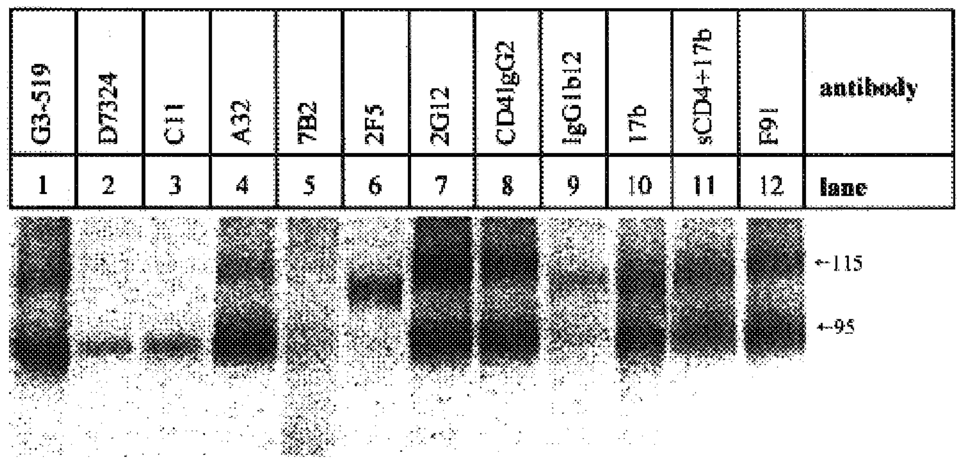
Figure 12B:
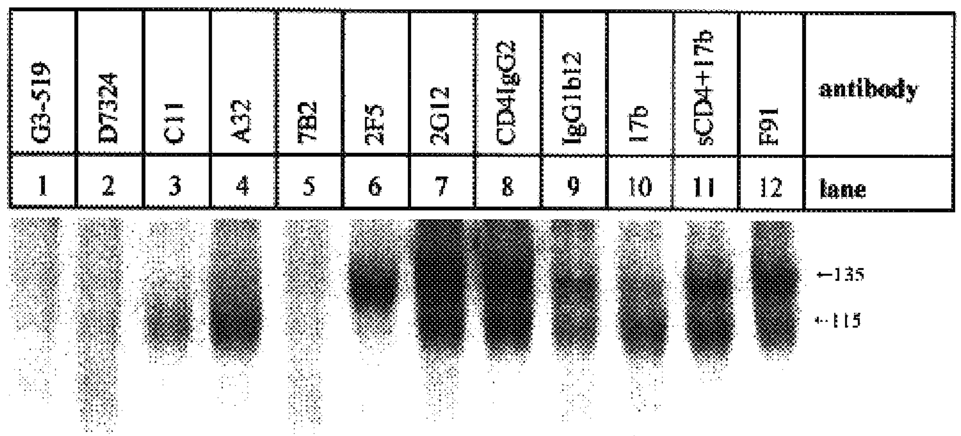

For each of the singly and doubly loop-deleted mutants, we could detect gp140 bands in comparable quantities as for the full-length SOS gp140 protein (FIG. 11B). To see whether deletion of the variable loops altered antigenicity in an oligomeric context, we precipitated the ΔV3 and ΔV1V2* SOS proteins with a panel of MAbs (FIG. 12). MAbs to gp41 except 2F5 did not bind to loop deleted versions of the cysteine stabilized protein, indicating that those epitopes are still occluded. MAbs to C1 and C5 epitopes were similarly non-reactive. The neutralizing antibody 2F5 did bind to the mutants and was particularly reactive with the ΔV3 SOS protein. MAbs to the CD4BS (IgG1b12, F91) as well as 2G12 bound avidly to these mutants as well. Of note is that CD4-IgG2 and 2G12 bound with very high affinity to the oligomeric ΔV3 SOS protein. Furthermore, consistent with data indicating that the CD4i epitopes are constitutively exposed on the ΔV1V2* protein, binding of MAbs 17b and A32 to the ΔV1V2* SOS mutant was not inducible by sCD4. The ΔV3 SOS mutant, however, bound 17b and A32 weakly in the absence of sCD4 and strongly in its presence. These results are consistent with observations that the V1/V2 and V3 loop structures are involved in occlusion of the CD4i epitopes (Wyatt et al., J. Virol. 69:5723, 1995). Taken together, the results demonstrate that variable loop-deleted gp140s can be disulfide-stabilized without loss of conformational integrity. FIGS. 14 and 15, respectively, contain the complete nucleic acid and amino acid sequences of the ΔV1V2* and ΔV3 JR-FL SOS proteins. For the ΔV1V2*V3 and ΔV1V2*V3 N357Q N398Q SOS mutants, we could not precipitate a gp140 (110 kDa and 105 kDa) with any of a variety of neutralizing and non-neutralizing MAbs (FIG. 11A, lanes 3, 4, 7 & 8). We did, however, observe strong 90 kDa and 85 kDa bands, which correspond to the mutant gp120 domains. These preliminary experiments suggest a variety of approaches for disulfide-stabilizing triply-loop deleted gp140s, including adjusting the location(s) of one or more introduced cysteines, adding additional pairs of cysteines, modifying amino acids adjacent to the introduced cysteines, and modifying the manner in which the loops are deleted. Alternatively, triply loop deleted gp140s derived from other HIV isolates may be more readily stabilized by cysteines introduced at residues homologous to 496/592.

7. Production and Purification of Recombinant HIV-1 Envelope Glycoproteins

Milligram quantities of high quality HIV-1 envelope glycoproteins are produced in CHO cells stably transfected with PPI4 envelope-expressing plasmids (U.S. Pat. Nos. 5,886,163 and 5,869,624). The PPI4 expression vector contains the dhfr gene under the control of the β-globin promoter. Selection in nucleoside-free media of $dhfr^{+}$ clones is followed by gene amplification using stepwise increases in methotrexate concentrations. The cytomegalovirus (CMV) promoter drives high level expression of the heterologous gene, and the tissue plasminogen activator signal sequence ensures efficient protein secretion. A high level of gp120 expression and secretion is obtained only upon inclusion of the complete 5' non-coding sequences of the CMV MIE gene up to and including the initiating ATG codon. To produce milligram quantities of protein, recombinant CHO cells are seeded into roller bottles in selective media and grown to confluency. Reduced serum-containing media is then used for the production phase, when supernatants are harvested twice weekly. A purification process comprising lectin affinity, ion exchange, and/or gel filtration chromatographies is carried out under non-denaturing conditions.

8. A Protocol for Determining the Immunogenicity of Stabilized HIV-1 Envelope Subunit Proteins Purified recombinant HIV-1 envelope proteins are formulated in suitable adjuvants (e.g., Alum or Ribi Detox). For alum, formulation is achieved by combining the mutant HIV-1 envelope glycoprotein (in phosphate buffered saline, normal saline or similar vehicle) with preformed aluminum hydroxide gel (Pierce, Rockford, Ill.) at a final concentration of approximately 500 μg/mL aluminum. The antigen is allowed to adsorb onto the alum gel for two hours at room temperature.

Guinea pigs or other animals are immunized 5 times, at monthly intervals, with approximately 100 μg of formulated antigen, by subcutaneous intramuscular or intraperitoneal routes. Sera from immunized animals are collected at biweekly intervals and tested for reactivity with HIV-1 envelope proteins in ELISA as described above and for neutralizing activity in well established HIV-1 infectivity assays (Trkola et al J. Virol 72: 1876, 1998). Vaccine candidates that elicit the highest levels of HIV-1 neutralizing Abs can be tested for immunogenicity and efficacy in preventing or treating infection in SHIV-macaque or other non-human primate models of HIV infection, as described below. The subunit vaccines could be used alone or in combination with other vaccine components, such as those designed to elicit a protective cellular immune response.

For these studies, the HIV-1 envelope proteins also may be administered in complex with one or more cellular HIV receptors, such as CD4, CCR5, and CXCR4. As described above, the binding of soluble CD4 exposes formerly cryptic conserved neutralization epitopes on the stabilized HIV-1 envelope protein. Antibodies raised to these or other neoepitopes could possess significant antiviral activity. As described above, interaction of CD4-env complexes with fusion coreceptors such as CCR5 and CXCR4 is thought to trigger additional conformational changes in env required for HIV fusion. Trivalent complexes comprising the stabilized env, CD4, and coreceptor could thus adopt additional fusion intermediary conformations, some of which are thought to be sufficiently long-lived for therapeutic and possibly immunologic interventions (Kilby et al. Nat. Med. 4:1302, 1998). Methods for preparing and administering env-CD4 and env-CD4-coreceptor complexes are well-known to the skilled artisan (LaCasse et al., Science 283:357, 1999; Kang et al., J. Virol., 68:5854, 1994; Gershoni et al., FASEB J. 7:1185, 1993).

9. A Protocol for Determining the Immunogenicity of Nucleic Acid-based Vaccines Encoding Stabilized HIV-1 Envelope Proteins Encoding the Stabilized HIV-1 Envelope Proteins PCR techniques are used to subclone the nucleic acid into a DNA vaccine plasmid vector such as pVAX1 available from Invitrogen (catalog #V260-20). PVAX1 was developed according to specifications in the FDA document "Points to Consider on Plasmid DNA Vaccines for Preventive Infectious Disease Indications" published on Dec. 22, 1996. PVAX1 has the following features: Eukaryotic DNA sequences are limited to those required for expression in order to minimize the possibility of chromosomal integration, Kanamycin is used to select the vector in *E.coli* because ampicillin has been reported to cause an allergic response in some individuals, Expression levels of recombinant proteins from pVAX1 is comparable to those achieved with its parent vector, pc DNA3.1, and the small size of pVAX1 and the variety of unique cloning sites amplify subcloning of even very large DNA fragments.

Several methods can be used to optimize expression of the disulfide stabilized protein in vivo. For example, standard PCR cloning techniques could be used to insert into pVAX1 certain elements of the optimized PPI4 expression vector, including Intron A and adjoining regions of the CMV promoter. In addition, the genomic DNA sequences of the HIV-1 envelope are biased towards codons that are suboptimal for expression in mammalian cells (Haas et al. Current Biol. 6:315, 1996). These can be changed to more favorable codons using standard mutagenesis techniques in order to improve the immunogenicity of nucleic acid based HIV vaccines (Andre et al., J. Virol. 72:1497, 1998). The codon optimization strategy could strive to increase the number of CpG motifs, which are known to increase the immunogencity of DNA vaccines (Klinman et al., J. Immunol. 158:3635, 1997). Lastly, as for the transient transfection systems described above, env processing into gp120-gp41 may be facilitated by the heterologous expression of furin introduced on the same or separate expression vectors.

The insert containing plasmid can be administered to the animals by such means as direct injection or using gene gun techniques. Such methods are known to those skilled in the art.

In one protocol, Rhesus macaques are individually inoculated with five approximately 1 mg doses of the nucleic acid. The doses are delivered at four week intervals. Each dose is administered intramuscularly. The doses are delivered at four week intervals. After four months, the animals receive a single immunization at two separate sites with 2 mg of nucleic acid with or without 300 μg of mutant HIV-1 envelope glycoprotein. This series may be followed by one or more subsequent recombinant protein subunit booster immunizations. The animals are bled at intervals of two to four weeks. Serum samples are prepared from each bleed to assay for the development of specific antibodies as described in the subsequent sections.

SHIV Challenge Experiments

Several chimeric HIV-SIV viruses have been created and characterized for infectivity in Rhesus monkeys. For Virus challenge experiments, the Rhesus monkeys are injected intravenously with a pre-titered dose of virus sufficient to infect greater than 9/10 animals. SHIV infection is determined by two assays. ELISA detection of SIV p27 antigen in monkey sera is determined using a commercially available kit (Coulter). Similarly, Western blot detection of anti-gag antibodies is performed using a commercially available kit (Cambridge Biotech).

A reduction in either the rate of infection or the amount of p27 antigen produced in immunized versus control monkeys would indicate that the vaccine or vaccine combination has prophylactic value.

What is claimed:

1. A nucleic acid encoding a modified viral env gene of a HIV-1 isolate, which gene comprises a nucleotide segment that encodes a modified form of a HIV-1 gp120 and gp41 complex, wherein the modifications comprise an A492C mutation in gp120 and a T596C mutation in gp41, such mutations being numbered by reference to the HIV-1 isolate JR-FL and the modifications resulting in a disulfide bond between gp120 and gp41 which stabilizes the otherwise non-covalent gp120-gp41 interaction, such stabilization resulting in enhanced binding of the disulfide-bonded gp120-gp41 complex to HIV-1 neutralizing antibodies and reduced binding of such complex to HIV-1 non-neutralizing antibodies.

2. A non-replicating viral vector comprising the nucleic acid of claim 1.

3. The nucleic acid of claim 1, wherein the HIV-1 isolate is HIV-$1_{JR-FL}$, HIV-$1_{DH123}$, HIV-$1_{Gun-1}$, HIV-$1_{89.6}$, or HIV-$1_{HXB2}$.

4. The nucleic acid of claim 1, wherein the modified gp120 is further characterized by the absence of one or more of the variable loops present in the wild type gp120.

5. The nucleic acid of claim 4, wherein the absent variable loop comprises V1, V2, V3 or a combination thereof.

6. The nucleic acid of claim 4, wherein the absent variable loop comprises V1 and V2.

7. The nucleic acid of claim 1, wherein the modified gp120 is further characterized by the absence or presence of one or more canonical glycosylation sites present or absent, respectively, in wild type gp120.

8. The nucleic acid of claim 7, wherein one or more canonical glycosylation sites are absent from the V1V2 region of the gp120.

9. The nucleic acid of claim 1, which is cDNA.

10. The nucleic acid of claim 1, which is genomic DNA.

11. The nucleic acid of claim 1, which is RNA.

12. A replicable vector comprising the nucleic acid of claim 1.

13. The replicable vector of claim 12 wherein the vector is a plasmid, cosmid, virus, viral vector, λ phage or YAC.

14. A host cell comprising the vector of claim 12.

15. The cell of claim 14, which is a eukaryotic cell.

16. The cell of claim 14, which is a bacterial cell.

17. A composition which comprises the nucleic acid of claim 1.

18. The composition of claim 17, wherein the composition comprises the nucleic acid in a DNA plasmid, a replicating viral vector, or a non-replicating viral vector.

19. A nucleic acid encoding a modified viral env gene of a HIV-1 isolate, which gene comprises a nucleotide segment that encodes a modified form of a HIV-1 gp120 and gp41 complex, wherein the modifications comprise a mutation in gp120 selected from the group consisting of V35C, Y39C, W44C, P484C, G486C, A488C, P489C, T490C, and A492C and a mutation in gp41 selected from the group consisting of D580C, W587C, T596C, V599C, P600C and W601C, such mutations being numbered by reference to the HIV-1 isolate JR-FL and the modifications resulting in a disulfide bond between gp120 and gp41 which stabilizes the otherwise non-covalent gp120-gp41 interaction.

20. A non-replicating viral vector comprising the nucleic acid of claim 19.

21. The nucleic acid of claim 19, wherein the modified gp120 is further characterized by the absence of one or more of the variable loops present in wild type gp120.

22. The nucleic acid of claim 21, wherein the absent variable loop comprises V1, V2, V3 or a combination thereof.

23. The nucleic acid of claim 21, wherein the absent variable loop comprises V1 and V2.

24. The nucleic acid of claim 19, wherein the modified gp120 is further characterized by the absence or presence of one or more canonical glycosylation sites present or absent, respectively, in wild type gp120.

25. The nucleic acid of claim 24, wherein one or more canonical glycosylation sites are absent from the V1V2 region of the gp120.

26. A replicable vector comprising the nucleic acid of claim 19.

27. A host cell comprising the vector of claim 26.

28. A composition which comprises the nucleic acid of claim 19.

29. The composition of claim 28, wherein the composition comprises the nucleic acid in a DNA plasmid, a replicating viral vector, or a non-replicating viral vector.

30. The nucleic acid of claim 19, wherein stabilization of the gp120-gp41 interaction results in enhanced binding of the disulfide-bonded gp120-gp41 complex to HIV-1 neutralizing antibodies and reduced binding of such complex to HIV-1 non-neutralizing antibodies.

* * * * *

SEQUENCE LISTING

```
<160> NUMBER OF SEQ ID NOS: 17

<210> SEQ ID NO 1
<211> LENGTH: 39
<212> TYPE: PRT
<213> ORGANISM: Human immunodeficiency virus type 1
```

-continued

<400> SEQUENCE: 1

Gly Gly Gly Asp Met Arg Asp Asn Trp Arg Ser Glu Leu Tyr Lys Tyr
1 5 10 15

Lys Val Val Lys Ile Glu Pro Leu Gly Val Ala Pro Thr Lys Ala Lys
20 25 30

Arg Arg Val Val Gln Arg Glu
35

<210> SEQ ID NO 2
<211> LENGTH: 100
<212> TYPE: PRT
<213> ORGANISM: Human immunodeficiency virus type 1

<400> SEQUENCE: 2

Val Glu Lys Leu Trp Val Thr Val Tyr Tyr Gly Val Pro Val Trp Lys
1 5 10 15

Glu Ala Thr Thr Thr Leu Phe Cys Ala Ser Asp Ala Lys Ala Tyr Asp
20 25 30

Thr Glu Val His Asn Val Trp Ala Thr His Ala Cys Val Pro Thr Asp
35 40 45

Pro Asn Pro Gln Glu Val Val Leu Glu Asn Val Thr Glu His Phe Asn
50 55 60

Met Trp Lys Asn Asn Met Val Glu Gln Met Gln Glu Asp Ile Ile Ser
65 70 75 80

Leu Trp Asp Gln Ser Leu Lys Pro Cys Val Lys Leu Thr Pro Leu Cys
85 90 95

Val Thr Leu Asn
100

<210> SEQ ID NO 3
<211> LENGTH: 32
<212> TYPE: DNA
<213> ORGANISM: Artificial sequence
<220> FEATURE:
<223> OTHER INFORMATION: primer directed to HIV-1

<400> SEQUENCE: 3
gtctattatg gggtacctga gaagctgtgg aa 32

<210> SEQ ID NO 4
<211> LENGTH: 36
<212> TYPE: DNA
<213> ORGANISM: ARTIFICIAL SEQUENCE
<220> FEATURE:
<223> OTHER INFORMATION: PRIMER DIRECTED TO HIV-1

<400> SEQUENCE: 4
cgcagacgca gattcgaatt aataccacag ccagtt 36

<210> SEQ ID NO 5
<211> LENGTH: 60
<212> TYPE: DNA
<213> ORGANISM: ARTIFICIAL SEQUENCE
<220> FEATURE:
<223> OTHER INFORMATION: PRIMER DIRECTED TO HIV-1

<400> SEQUENCE: 5
ctacgacttc gtctccgcct tcgactacgg ggaataggag ctgtgttcct tgggttcttg 60

<210> SEQ ID NO 6

-continued

<211> LENGTH: 60
<212> TYPE: DNA
<213> ORGANISM: ARTIFICIAL SEQUENCE
<220> FEATURE:
<223> OTHER INFORMATION: PRIMER DIRECTED TO HIV-1

<400> SEQUENCE: 6
tcgaaggcgg agacgaagtc gtagccgcag tgccttggtg ggtgctactc ctaatggttc 60

<210> SEQ ID NO 7
<211> LENGTH: 32
<212> TYPE: DNA
<213> ORGANISM: ARTIFICIAL SEQUENCE
<220> FEATURE:
<223> OTHER INFORMATION: PRIMER DIRECTED TO HIV-1

<400> SEQUENCE: 7
gtctattatg gggtacctgt gtggaaagaa gc 32

<210> SEQ ID NO 8
<211> LENGTH: 39
<212> TYPE: DNA
<213> ORGANISM: ARTIFICIAL SEQUENCE
<220> FEATURE:
<223> OTHER INFORMATION: PRIMER DIRECTED TO ENVELOPE PROTEIN

<400> SEQUENCE: 8
gtctgagtcg gatcctgtga cacctcagtc attacacag 39

<210> SEQ ID NO 9
<211> LENGTH: 60
<212> TYPE: DNA
<213> ORGANISM: ARTIFICIAL SEQUENCE
<220> FEATURE:
<223> OTHER INFORMATION: PRIMER DIRECTED TO ENVELOPE PROTEIN

<400> SEQUENCE: 9
ctcgagtctt cgaattagtg atgggtgatg gtgatgatac cacagccatt ttgttatgtc 60

<210> SEQ ID NO 10
<211> LENGTH: 87
<212> TYPE: DNA
<213> ORGANISM: ARTIFICIAL SEQUENCE
<220> FEATURE:
<223> OTHER INFORMATION: PRIMER DIRECTED TO ENVELOPE PROTEIN

<400> SEQUENCE: 10
ggctcaaagg atatctttgg acaggcctgt gtaatgactg aggtgtcaca tcctgcacca 60
cagagtgggg ttaattttac acatggc 87

<210> SEQ ID NO 11
<211> LENGTH: 15
<212> TYPE: PRT
<213> ORGANISM: Human immunodeficiency virus type 1

<400> SEQUENCE: 11

Ala Pro Thr Lys Ala Lys Arg Arg Val Val Gln Arg Glu Lys Arg
1 5 10 15

<210> SEQ ID NO 12
<211> LENGTH: 1929
<212> TYPE: DNA
<213> ORGANISM: Human immunodeficiency virus type 1

<400> SEQUENCE: 12

-continued

```
gtagaaaagt tgtgggtcac agtctattat ggggtacctg tgtggaaaga agcaaccacc      60
actctatttt gtgcatcaga tgctaaagca tatgatacag aggtacataa tgtttgggcc     120
acacatgcct gtgtacccac agaccccaac ccacaagaag tagtattgga aaatgtaaca     180
gaacatttta acatgtggaa aaataacatg gtagaacaga tgcaggagga tataatcagt     240
ttatgggatc aaagcctaaa gccatgtgta aaattaaccc cactctgtgt tactttaaat     300
tgcaaggatg tgaatgctac taataccact aatgatagcg agggaacgat ggagagagga     360
gaaataaaaa actgctcttt caatatcacc acaagcataa gagatgaggt gcagaaagaa     420
tatgctcttt tttataaact tgatgtagta ccaatagata ataataatac cagctatagg     480
ttgataagtt gtgacacctc agtcattaca caggcctgtc caaagatatc ctttgagcca     540
attcccatac attattgtgc cccggctggt tttgcgattc taaagtgtaa tgataagacg     600
ttcaatggaa aaggaccatg taaaaatgtc agcacagtac aatgtacaca tggaattagg     660
ccagtagtat caactcaact gctgctaaat ggcagtctag cagaagaaga ggtagtaatt     720
agatctgaca atttcacgaa caatgctaaa accataatag tacagctgaa agaatctgta     780
gaaattaatt gtacaagacc caacaacaat acaagaaaaa gtatacatat aggaccaggg     840
agagcatttt atactacagg agaaataata ggagatataa gacaagcaca ttgtaacatt     900
agtagagcaa aatggaatga cactttaaaa cagatagtta taaaattaag agaacaattt     960
gagaataaaa caatagtctt taatcactcc tcaggagggg acccagaaat tgtaatgcac    1020
agttttaatt gtgaaggaga atttttctac tgtaattcaa cacaactgtt taatagtact    1080
tggaataata atactgaagg gtcaaataac actgaaggaa atactatcac actcccatgc    1140
agaataaaac aaattataaa catgtggcag gaagtaggaa aagcaatgta tgcccctccc    1200
atcagaggac aaattagatg ttcatcaaat attacagggc tgctattaac aagagatggt    1260
ggtattaatg agaatgggac cgagatcttc agacctggag gaggagatat gagggacaat    1320
tggagaagtg aattctataa atataaagta gtaaaaattg aaccattagg agtagcaccc    1380
accaagtgca agagaagagt ggtgcaaaga gaaaaaagag cagtgggaat aggagctgtg    1440
ttccttgggt tcttgggagc agcaggaagc actatgggcg cagcgtcaat gacactgacg    1500
gtacaggcca gactattatt gtctggtata gtgcaacagc agaacaattt gctgagggct    1560
attgaggcgc aacagcgtat gttgcaactc acagtctggg gcatcaagca gctccaggca    1620
agagtcctgg ctgtggaaag atacctaggg gatcaacagc tcctggggat ttggggttgc    1680
tctggaaaac tcatttgctg cactgctgtg ccttggaatg ctagttggag taataaatct    1740
ctagatagga tttggaataa catgacctgg atggagtggg aaagagaaat tgacaattac    1800
acaagcgaaa tatacacact aattgaagaa tcgcagaacc aacaagaaaa gaatgaacaa    1860
gaattattgg aattagataa atgggcaagt ttgtggaatt ggtttgacat aacaaactgg    1920
ctgtggtat                                                            1929
```

<210> SEQ ID NO 13
<211> LENGTH: 643
<212> TYPE: PRT
<213> ORGANISM: Human immunodeficiency virus type 1

<400> SEQUENCE: 13

```
Val Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30
```

-continued

```
Thr Glu Val His Asn Val Trp Ala Thr His Ala Cys Val Pro Thr Asp
        35                  40                  45

Pro Asn Pro Gln Glu Val Val Leu Glu Asn Val Thr Glu His Phe Asn
    50                  55                  60

Met Trp Lys Asn Asn Met Val Glu Gln Met Gln Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Lys Asp Val Asn Ala Thr Asn Thr Thr Asn Asp
            100                 105                 110

Ser Glu Gly Thr Met Glu Arg Gly Glu Ile Lys Asn Cys Ser Phe Asn
        115                 120                 125

Ile Thr Thr Ser Ile Arg Asp Glu Val Gln Lys Glu Tyr Ala Leu Phe
    130                 135                 140

Tyr Lys Leu Asp Val Val Pro Ile Asp Asn Asn Asn Thr Ser Tyr Arg
145                 150                 155                 160

Leu Ile Ser Cys Asp Thr Ser Val Ile Thr Gln Ala Cys Pro Lys Ile
                165                 170                 175

Ser Phe Glu Pro Ile Pro Ile His Tyr Cys Ala Pro Ala Gly Phe Ala
            180                 185                 190

Ile Leu Lys Cys Asn Asp Lys Thr Phe Asn Gly Lys Gly Pro Cys Lys
        195                 200                 205

Asn Val Ser Thr Val Gln Cys Thr His Gly Ile Arg Pro Val Val Ser
    210                 215                 220

Thr Gln Leu Leu Leu Asn Gly Ser Leu Ala Glu Glu Glu Val Val Ile
225                 230                 235                 240

Arg Ser Asp Asn Phe Thr Asn Asn Ala Lys Thr Ile Ile Val Gln Leu
                245                 250                 255

Lys Glu Ser Val Glu Ile Asn Cys Thr Arg Pro Asn Asn Asn Thr Arg
            260                 265                 270

Lys Ser Ile His Ile Gly Pro Gly Arg Ala Phe Tyr Thr Thr Gly Glu
        275                 280                 285

Ile Ile Gly Asp Ile Arg Gln Ala His Cys Asn Ile Ser Arg Ala Lys
    290                 295                 300

Trp Asn Asp Thr Leu Lys Gln Ile Val Ile Lys Leu Arg Glu Gln Phe
305                 310                 315                 320

Glu Asn Lys Thr Ile Val Phe Asn His Ser Ser Gly Gly Asp Pro Glu
                325                 330                 335

Ile Val Met His Ser Phe Asn Cys Glu Gly Glu Phe Phe Tyr Cys Asn
            340                 345                 350

Ser Thr Gln Leu Phe Asn Ser Thr Trp Asn Asn Asn Thr Glu Gly Ser
        355                 360                 365

Asn Asn Thr Glu Gly Asn Thr Ile Thr Leu Pro Cys Arg Ile Lys Gln
    370                 375                 380

Ile Ile Asn Met Trp Gln Glu Val Gly Lys Ala Met Tyr Ala Pro Pro
385                 390                 395                 400

Ile Arg Gly Gln Ile Arg Cys Ser Ser Asn Ile Thr Gly Leu Leu Leu
                405                 410                 415

Thr Arg Asp Gly Gly Ile Asn Glu Asn Gly Thr Glu Ile Phe Arg Pro
            420                 425                 430

Gly Gly Gly Asp Met Arg Asp Asn Trp Arg Ser Glu Phe Tyr Lys Tyr
        435                 440                 445
```

-continued

```
Lys Val Val Lys Ile Glu Pro Leu Gly Val Ala Pro Thr Lys Cys Lys
    450                 455                 460

Arg Arg Val Val Gln Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
                485                 490                 495

Met Thr Leu Thr Val Gln Ala Arg Leu Leu Leu Ser Gly Ile Val Gln
            500                 505                 510

Gln Gln Asn Asn Leu Leu Arg Ala Ile Glu Ala Gln Gln Arg Met Leu
        515                 520                 525

Gln Leu Thr Val Trp Gly Ile Lys Gln Leu Gln Ala Arg Val Leu Ala
    530                 535                 540

Val Glu Arg Tyr Leu Gly Asp Gln Gln Leu Leu Gly Ile Trp Gly Cys
545                 550                 555                 560

Ser Gly Lys Leu Ile Cys Cys Thr Ala Val Pro Trp Asn Ala Ser Trp
                565                 570                 575

Ser Asn Lys Ser Leu Asp Arg Ile Trp Asn Asn Met Thr Trp Met Glu
            580                 585                 590

Trp Glu Arg Glu Ile Asp Asn Tyr Thr Ser Glu Ile Tyr Thr Leu Ile
        595                 600                 605

Glu Glu Ser Gln Asn Gln Gln Glu Lys Asn Glu Gln Glu Leu Leu Glu
    610                 615                 620

Leu Asp Lys Trp Ala Ser Leu Trp Asn Trp Phe Asp Ile Thr Asn Trp
625                 630                 635                 640

Leu Trp Tyr
```

<210> SEQ ID NO 14
<211> LENGTH: 1738
<212> TYPE: DNA
<213> ORGANISM: Human immunodeficiency virus type 1

<400> SEQUENCE: 14

```
agtagaaaag ttgtgggtca cagtctatta tggggtacct gtgtggaaag aagcaaccac      60

cactctattt tgtgcatcag atgctaaagc atatgataca gaggtacata atgtttgggc     120

cacacatgcc tgtgtaccca cagaccccaa cccacaagaa gtagtattgg aaaatgtaac     180

agaacatttt aacatgtgga aaaataacat ggtagaacag atgcaggagg atataatcag     240

tttatgggat caaagcctaa agccatgtgt aaaattaacc ccactctgtg gtgcaggatg     300

tgacacctca gtcattacac aggcctgtcc aaagatatcc tttgagccaa ttcccataca     360

ttattgtgcc ccggctggtt ttgcgattct aaagtgtaat gataagacgt tcaatggaaa     420

aggaccatgt aaaaatgtca gcacagtaca atgtacacat ggaattaggc cagtagtatc     480

aactcaactg ctgctaaatg gcagtctagc agaagaagag gtagtaatta gatctgacaa     540

tttcacgaac aatgctaaaa ccataatagt acagctgaaa gaatctgtag aaattaattg     600

tacaagaccc aacaacaata caagaaaaag tatacatata ggaccaggga gagcatttta     660

tactacagga gaaataatag gagatataag acaagcacat tgtaacatta gtagagcaaa     720

atggaatgac actttaaaac agatagttat aaaattaaga gaacaatttg agaataaaac     780

aatagtcttt aatcactcct caggagggga cccagaaatt gtaatgcaca gttttaattg     840

tggaggagaa tttttctact gtaattcaac acaactgttt aatagtactt ggaataataa     900

tactgaaggg tcaaataaca ctgaaggaaa tactatcaca ctcccatgca gaataaaaca     960

aattataaac atgtggcagg aagtaggaaa agcaatgtat gcccctccca tcagaggaca    1020
```

```
aattagatgt tcatcaaata ttacagggct gctattaaca agagatggtg gtattaatga   1080

gaatgggacc gagatcttca gacctggagg aggagatatg agggacaatt ggagaagtga   1140

attatataaa tataaagtag taaaaattga accattagga gtagcaccca ccaagtgcaa   1200

gagaagagtg gtgcaaagag aaaaaagagc agtgggaata ggagctgtgt tccttgggtt   1260

cttgggagca gcaggaagca ctatgggcgc agcgtcaatg acactgacgg tacaggccag   1320

actattattg tctggtatag tgcaacagca gaacaatttg ctgagggcta ttgaggcgca   1380

acagcgtatg ttgcaactca cagtctgggg catcaagcag ctccaggcaa gagtcctggc   1440

tgtggaaaga tacctagggg atcaacagct cctggggatt tggggttgct ctggaaaact   1500

catttgctgc actgctgtgc cttggaatgc tagttggagt aataaatctc tggataggat   1560

ttggaataac atgacctgga tggagtggga aagagaaatt gacaattaca caagcgaaat   1620

atacacccta attgaagaat cgcagaacca acaagaaaag aatgaacaag aattattgga   1680

attagataaa tgggcaagtt tgtggaattg gtttgacata acaaactggc tgtggtat     1738

<210> SEQ ID NO 15
<211> LENGTH: 579
<212> TYPE: PRT
<213> ORGANISM: Human immunodeficiency virus type 1

<400> SEQUENCE: 15

Val Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu His Phe Asn
    50                  55                  60

Met Trp Lys Asn Asn Met Val Glu Gln Met Gln Glu Asp Ile Ile Ser
65                  70                  75                  80

Leu Trp Asp Gln Ser Leu Lys Pro Cys Val Lys Leu Thr Pro Leu Cys
                85                  90                  95

Gly Ala Gly Cys Asp Thr Ser Val Ile Thr Gln Ala Cys Pro Lys Ile
            100                 105                 110

Ser Phe Glu Pro Ile Pro Ile His Tyr Cys Ala Pro Ala Gly Phe Ala
        115                 120                 125

Ile Leu Lys Cys Asn Asp Lys Thr Phe Asn Gly Lys Gly Pro Cys Lys
    130                 135                 140

Asn Val Ser Thr Val Gln Cys Thr His Gly Ile Arg Pro Val Val Ser
145                 150                 155                 160

Thr Gln Leu Leu Leu Asn Gly Ser Leu Ala Glu Glu Glu Val Val Ile
                165                 170                 175

Arg Ser Asp Asn Phe Thr Asn Asn Ala Lys Thr Ile Ile Val Gln Leu
            180                 185                 190

Lys Glu Ser Val Glu Ile Asn Cys Thr Arg Pro Asn Asn Asn Thr Arg
        195                 200                 205

Lys Ser Ile His Ile Gly Pro Gly Arg Ala Phe Tyr Thr Thr Gly Glu
    210                 215                 220

Ile Ile Gly Asp Ile Arg Gln Ala His Cys Asn Ile Ser Arg Ala Lys
225                 230                 235                 240

Trp Asn Asp Thr Leu Lys Gln Ile Val Ile Lys Leu Arg Glu Gln Phe
```

-continued

```
                245                 250                 255

Glu Asn Lys Thr Ile Val Phe Asn His Ser Ser Gly Gly Asp Pro Glu
            260                 265                 270

Ile Val Met His Ser Phe Asn Cys Gly Gly Glu Phe Phe Tyr Cys Asn
        275                 280                 285

Ser Thr Gln Leu Phe Asn Ser Thr Trp Asn Asn Asn Thr Glu Gly Ser
    290                 295                 300

Asn Asn Thr Glu Gly Asn Thr Ile Thr Leu Pro Cys Arg Ile Lys Gln
305                 310                 315                 320

Ile Ile Asn Met Trp Gln Glu Val Gly Lys Ala Met Tyr Ala Pro Pro
                325                 330                 335

Ile Arg Gly Gln Ile Arg Cys Ser Ser Asn Ile Thr Gly Leu Leu Leu
            340                 345                 350

Thr Arg Asp Gly Gly Ile Asn Glu Asn Gly Thr Glu Ile Phe Arg Pro
        355                 360                 365

Gly Gly Gly Asp Met Arg Asp Asn Trp Arg Ser Glu Leu Tyr Lys Tyr
    370                 375                 380

Lys Val Val Lys Ile Glu Pro Leu Gly Val Ala Pro Thr Lys Cys Lys
385                 390                 395                 400

Arg Arg Val Val Gln Arg Glu Lys Arg Ala Val Gly Ile Gly Ala Val
                405                 410                 415

Phe Leu Gly Phe Leu Gly Ala Ala Gly Ser Thr Met Gly Ala Ala Ser
            420                 425                 430

Met Thr Leu Thr Val Gln Ala Arg Leu Leu Leu Ser Gly Ile Val Gln
        435                 440                 445

Gln Gln Asn Asn Leu Leu Arg Ala Ile Glu Ala Gln Gln Arg Met Leu
    450                 455                 460

Gln Leu Thr Val Trp Gly Ile Lys Gln Leu Gln Ala Arg Val Leu Ala
465                 470                 475                 480

Val Glu Arg Tyr Leu Gly Asp Gln Gln Leu Leu Gly Ile Trp Gly Cys
                485                 490                 495

Ser Gly Lys Leu Ile Cys Cys Thr Ala Val Pro Trp Asn Ala Ser Trp
            500                 505                 510

Ser Asn Lys Ser Leu Asp Arg Ile Trp Asn Asn Met Thr Trp Met Glu
        515                 520                 525

Trp Glu Arg Glu Ile Asp Asn Tyr Thr Ser Glu Ile Tyr Thr Leu Ile
    530                 535                 540

Glu Glu Ser Gln Asn Gln Gln Glu Lys Asn Glu Gln Glu Leu Leu Glu
545                 550                 555                 560

Leu Asp Lys Trp Ala Ser Leu Trp Asn Trp Phe Asp Ile Thr Asn Trp
                565                 570                 575

Leu Trp Tyr
```

<210> SEQ ID NO 16
<211> LENGTH: 1875
<212> TYPE: DNA
<213> ORGANISM: Human immunodeficiency virus type 1
<220> FEATURE:
<221> NAME/KEY: misc_feature
<222> LOCATION: (453)..(453)
<223> OTHER INFORMATION: n=unknown
<220> FEATURE:
<221> NAME/KEY: misc_feature
<222> LOCATION: (615)..(615)
<223> OTHER INFORMATION: n=unknown
<220> FEATURE:
<221> NAME/KEY: misc_feature
<222> LOCATION: (639)..(639)
<223> OTHER INFORMATION: n=unknown

<400> SEQUENCE: 16

```
gtagaaaagt tgtgggtcac agtctattat ggggtacctg tgtggaaaga agcaaccacc     60
actctatttt gtgcatcaga tgctaaagca tatgatacag aggtacataa tgtttgggcc    120
acacatgcct gtgtacccac agaccccaac ccacaagaag tagtattgga aaatgtaaca    180
gaacatttta acatgtggaa aaataacatg gtagaacaga tgcaggagga tataatcagt    240
ttatgggatc aaagcctaaa gccatgtgta aaattaaccc cactctgtgt tactttaaat    300
tgcaaggatg tgaatgctac taataccact aatgatagcg agggaacgat ggagagagga    360
gaaataaaaa actgctcttt caatatcacc acaagcataa gagatgaggt gcagaaagaa    420
tatgctcttt tttataaact tgatgtagta ccnatagata ataataatac cagctatagg    480
ttgataagtt gtgacacctc agtcattaca caggcctgtc caaagatatc ctttgagcca    540
attcccatac attattgtgc cccggctggt tttgcgattc taaagtgtaa tgataagacg    600
ttcaatggaa aaggnccatg taaaaatgtc agcacagtnc aatgtacaca tggaattagg    660
ccagtagtat caactcaact gctgctaaat ggcagtctag cagaagaaga ggtagtaatt    720
agatctgaca atttcacgaa caatgctaaa accataatag tacagctgaa agaatctgta    780
gaaattaatt gtacaagacc caacaacaat ggagccggcg atataagaca agcacattgt    840
aacattagta gagcaaaatg gaatgacact ttaaaacaga tagttataaa attaagagaa    900
caatttgaga ataaaacaat agtctttaat cactcctcag gaggggaccc agaaattgta    960
atgcacagtt ttaattgtgg aggagaattt ttctactgta attcaacaca actgtttaat   1020
agtacttgga ataataatac tgaagggtca aataacactg aaggaaatac tatcacactc   1080
ccatgcagaa taaaacaaat tataaacatg tggcaggaag taggaaaagc aatgtatgcc   1140
cctcccatca gaggacaaat tagatgttca tcaaatatta cagggctgct attaacaaga   1200
gatggtggta ttaatgagaa tgggaccgag atcttcagac ctggaggagg agatatgagg   1260
gacaattgga gaagtgaatt atataaatat aaagtagtaa aaattgaacc attaggagta   1320
gcacccacca agtgcaagag aagagtggtg caaagagaaa aaagagcagt gggaatagga   1380
gctgtgttcc ttgggttctt gggagcagca ggaagcacta tgggcgcagc gtcaatgaca   1440
ctgacggtac aggccagact attattgtct ggtatagtgc aacagcagaa caatttgctg   1500
agggctattg aggcgcaaca gcgtatgttg caactcacag tctggggcat caagcagctc   1560
caggcaagag tcctggctgt ggaaagatac ctaggggatc aacagctcct ggggatttgg   1620
ggttgctctg gaaaactcat ttgctgcact gctgtgcctt ggaatgctag ttggagtaat   1680
aaatctctgg ataggatttg gaataacatg acctggatgg agtgggaaag agaaattgac   1740
aattacacaa gcgaaatata caccctaatt gaagaatcgc agaaccaaca agaaaagaat   1800
gaacaagaat tattggaatt agataaatgg gcaagtttgt ggaattggtt tgacataaca   1860
aaatggctgt ggtat                                                    1875
```

<210> SEQ ID NO 17
<211> LENGTH: 625
<212> TYPE: PRT
<213> ORGANISM: Human immunodeficiency virus type 1
<220> FEATURE:
<221> NAME/KEY: MISC_FEATURE
<222> LOCATION: (151)..(151)
<223> OTHER INFORMATION: X=UNKNOWN AMINO ACID
<220> FEATURE:

-continued

<221> NAME/KEY: MISC_FEATURE
<222> LOCATION: (205)..(205)
<223> OTHER INFORMATION: X=UNKNOWN AMINO ACID
<220> FEATURE:
<221> NAME/KEY: MISC_FEATURE
<222> LOCATION: (213)..(213)
<223> OTHER INFORMATION: X=UNKNOWN AMINO ACID

<400> SEQUENCE: 17

```
Val Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu His Phe Asn
    50                  55                  60

Met Trp Lys Asn Asn Met Val Glu Gln Met Gln Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Lys Asp Val Asn Ala Thr Asn Thr Thr Asn Asp
            100                 105                 110

Ser Glu Gly Thr Met Glu Arg Gly Glu Ile Lys Asn Cys Ser Phe Asn
        115                 120                 125

Ile Thr Thr Ser Ile Arg Asp Glu Val Gln Lys Glu Tyr Ala Leu Phe
    130                 135                 140

Tyr Lys Leu Asp Val Val Xaa Ile Asp Asn Asn Asn Thr Ser Tyr Arg
145                 150                 155                 160

Leu Ile Ser Cys Asp Thr Ser Val Ile Thr Gln Ala Cys Pro Lys Ile
                165                 170                 175

Ser Phe Glu Pro Ile Pro Ile His Tyr Cys Ala Pro Ala Gly Phe Ala
            180                 185                 190

Ile Leu Lys Cys Asn Asp Lys Thr Phe Asn Gly Lys Xaa Pro Cys Lys
        195                 200                 205

Asn Val Ser Thr Xaa Gln Cys Thr His Gly Ile Arg Pro Val Val Ser
    210                 215                 220

Thr Gln Leu Leu Leu Asn Gly Ser Leu Ala Glu Glu Glu Val Val Ile
225                 230                 235                 240

Arg Ser Asp Asn Phe Thr Asn Asn Ala Lys Thr Ile Ile Val Gln Leu
                245                 250                 255

Lys Glu Ser Val Glu Ile Asn Cys Thr Arg Pro Asn Asn Asn Gly Ala
            260                 265                 270

Gly Asp Ile Arg Gln Ala His Cys Asn Ile Ser Arg Ala Lys Trp Asn
        275                 280                 285

Asp Thr Leu Lys Gln Ile Val Ile Lys Leu Arg Glu Gln Phe Glu Asn
    290                 295                 300

Lys Thr Ile Val Phe Asn His Ser Ser Gly Gly Asp Pro Glu Ile Val
305                 310                 315                 320

Met His Ser Phe Asn Cys Gly Gly Glu Phe Phe Tyr Cys Asn Ser Thr
                325                 330                 335

Gln Leu Phe Asn Ser Thr Trp Asn Asn Asn Thr Glu Gly Ser Asn Asn
            340                 345                 350

Thr Glu Gly Asn Thr Ile Thr Leu Pro Cys Arg Ile Lys Gln Ile Ile
        355                 360                 365
```

-continued

```
Asn Met Trp Gln Glu Val Gly Lys Ala Met Tyr Ala Pro Pro Ile Arg
    370                 375                 380

Gly Gln Ile Arg Cys Ser Ser Asn Ile Thr Gly Leu Leu Leu Thr Arg
385                 390                 395                 400

Asp Gly Gly Ile Asn Glu Asn Gly Thr Glu Ile Phe Arg Pro Gly Gly
                405                 410                 415

Gly Asp Met Arg Asp Asn Trp Arg Ser Glu Leu Tyr Lys Tyr Lys Val
            420                 425                 430

Val Lys Ile Glu Pro Leu Gly Val Ala Pro Thr Lys Cys Lys Arg Arg
        435                 440                 445

Val Val Gln Arg Glu Lys Arg Ala Val Gly Ile Gly Ala Val Phe Leu
    450                 455                 460

Gly Phe Leu Gly Ala Ala Gly Ser Thr Met Gly Ala Ala Ser Met Thr
465                 470                 475                 480

Leu Thr Val Gln Ala Arg Leu Leu Leu Ser Gly Ile Val Gln Gln Gln
                485                 490                 495

Asn Asn Leu Leu Arg Ala Ile Glu Ala Gln Gln Arg Met Leu Gln Leu
            500                 505                 510

Thr Val Trp Gly Ile Lys Gln Leu Gln Ala Arg Val Leu Ala Val Glu
        515                 520                 525

Arg Tyr Leu Gly Asp Gln Gln Leu Leu Gly Ile Trp Gly Cys Ser Gly
    530                 535                 540

Lys Leu Ile Cys Cys Thr Ala Val Pro Trp Asn Ala Ser Trp Ser Asn
545                 550                 555                 560

Lys Ser Leu Asp Arg Ile Trp Asn Asn Met Thr Trp Met Glu Trp Glu
                565                 570                 575

Arg Glu Ile Asp Asn Tyr Thr Ser Glu Ile Tyr Thr Leu Ile Glu Glu
            580                 585                 590

Ser Gln Asn Gln Gln Glu Lys Asn Glu Gln Glu Leu Leu Glu Leu Asp
        595                 600                 605

Lys Trp Ala Ser Leu Trp Asn Trp Phe Asp Ile Thr Lys Trp Leu Trp
    610                 615                 620

Tyr
625
```